United States Patent
Borden et al.

(10) Patent No.: US 6,426,644 B1
(45) Date of Patent: Jul. 30, 2002

(54) APPARATUS AND METHOD FOR DETERMINING THE ACTIVE DOPANT PROFILE IN A SEMICONDUCTOR WAFER

(75) Inventors: Peter G. Borden, San Mateo; Regina G. Nijmeijer, Mountain View, both of CA (US)

(73) Assignee: Boxer Cross Inc., Menlo Park, CA (US)

(*) Notice: Subject to any disclaimer, the term of this patent is extended or adjusted under 35 U.S.C. 154(b) by 0 days.

(21) Appl. No.: 09/935,128

(22) Filed: Aug. 21, 2001

Related U.S. Application Data

(62) Division of application No. 09/274,821, filed on Mar. 22, 1999, now Pat. No. 6,323,951.

(51) Int. Cl.[7] ............... G01R 31/26; G01N 21/41
(52) U.S. Cl. ............... 324/765; 324/752; 324/766; 356/445
(58) Field of Search ............... 324/765, 501, 324/752, 766, 767; 703/13, 14, 20; 356/432, 433, 445, 502; 438/14, 17

(56) References Cited

U.S. PATENT DOCUMENTS

| | | | |
|---|---|---|---|
| 4,996,659 A | * 2/1991 | Yamaguchi et al. | 714/736 |
| 5,042,952 A | 8/1991 | Opsal et al. | 356/432 |
| 5,377,006 A | 12/1994 | Nakata | 356/349 |
| 5,652,716 A | * 7/1997 | Battersby | 703/13 |
| 5,706,094 A | 1/1998 | Maris | 356/432 |
| 5,761,082 A | * 6/1998 | Miura-Mattausch | 703/14 |
| 6,118,533 A | 9/2000 | Banet et al. | 356/345 |

* cited by examiner

Primary Examiner—Ernest Karlsen
(74) Attorney, Agent, or Firm—Omkar Suryadevara; Silicon Valley Patent Group LLP

(57) ABSTRACT

A method (1) creates charge carriers in a concentration that changes in a periodic manner (also called "modulation") only with respect to time, and (2) determines the umber of charge carriers created in the carrier creation region by measuring an interference signal obtained by interference between a reference beam and a portion of a probe beam that is reflected by charge carriers at various depths of the semiconductor material, and comparing the measurement with corresponding values obtained by simulation (e.g. in graphs of such measurements for different junction depths). Various properties of the reflected portion of the probe beam (such as power and phase) are functions of the depth at which the reflection occurs, and can be measured to determine the depth of the junction, and the profile of active dopants. Therefore, the just-described reflected portion of the probe beam is interfered with a reference beam formed by a portion of probe beam reflected by the front surface of the semiconductor material, and phase and amplitude of the interference signal resulting therefrom are both measured. Alternatively, phase difference between a first interference signal (obtained by interference of (1) a variable phase beam and (2) the portion of probe beam reflected by the front surface) and a second interference signal (obtained by interference of (1) the variable phase beam and (2) a portion of the probe beam reflected by charge carriers at various depths) indicates the junction depth.

10 Claims, 14 Drawing Sheets

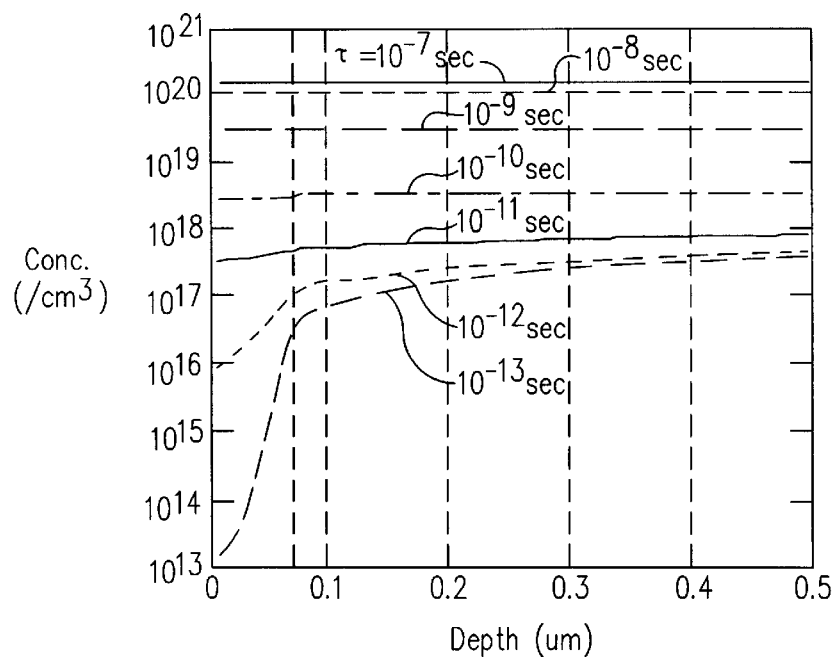
FIG. 9A
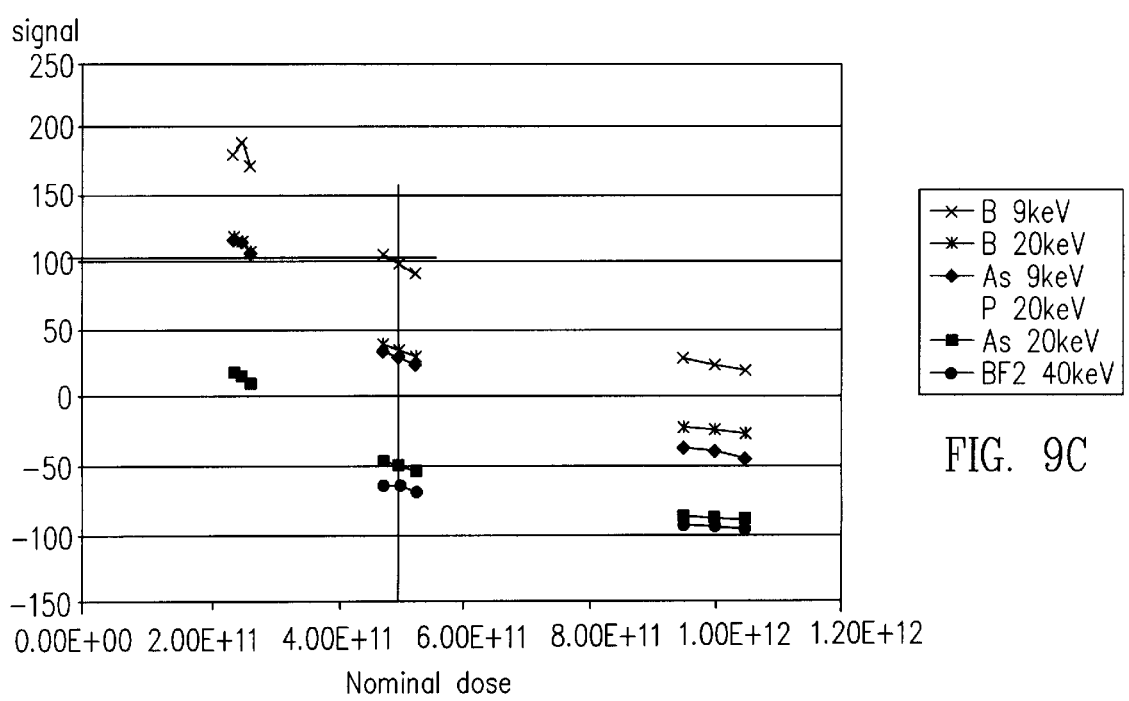
FIG. 9B
FIG. 9C

APPARATUS AND METHOD FOR DETERMINING THE ACTIVE DOPANT PROFILE IN A SEMICONDUCTOR WAFER

CROSS-REFERENCES TO RELATED APPLICATIONS

This Application is a divisional application from U.S. patent application Ser. No. 09/274,821, which was filed on Mar. 22, 1999, now U.S. Pat. No. 6,323,951.

This application is related to and incorporates by reference in their entirety the following three commonly owned and copending U.S. patent applications:

Ser. No. 08/638,944, entitled "SYSTEM AND METHOD FOR MEASURING THE DOPING LEVEL AND DOPING PROFILE OF A REGION IN A SEMICONDUCTOR SUBSTRATE" and filed on Apr. 24, 1996 by Peter G. Borden, now U.S. Pat. No. 5,883,518 issued on Mar. 16, 1999;

Ser. No. 08/637,244, entitled "SYSTEM AND METHOD FOR MEASURING PROPERTIES OF A SEMICONDUCTOR SUBSTRATE IN A FABRICATION LINE" and filed on Apr. 24, 1996 by Peter G. Borden, now U.S. Pat. No. 5,966,019 issued on Oct. 12,1999; and Ser. No. 09/095,804, entitled "AN APPARATUS AND METHOD FOR EVALUATING A WAFER OF SEMICONDUCTOR MATERIAL" and filed on Jun. 10, 1998 by Peter G. Borden et al., now U.S. Pat. No. 6,049,220 issued on Apr. 11, 2000.

CROSS REFERENCE TO SOFTWARE APPENDIX

Appendix A, included herein as pages 54–62, is a listing of computer programs and related data for use with Visual Basic software version 5.0, 1997, available from Microsoft Corporation. The software may be loaded into a personal computer for implementing a method and apparatus as described below in reference to FIGS. 4A–4F in one illustrative embodiment of this invention.

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

DISCUSSION OF THE RELATED ART

In the processing of a semiconductor wafer to form integrated circuits, charged atoms or molecules are directly introduced into the wafer in a process called ion implantation. Ion implantation normally causes damage to the lattice structure of the wafer, and to remove the damage, the wafer is normally annealed at an elevated temperature, typically 600° C. to 1100° C. This anneal also causes implanted atoms to move from interstitial sites to substitutional sites in the crystal lattice (an atom must be in a substitutional site to be electrically active). Prior to annealing, material properties at the surface of the wafer may be measured, specifically by using the damage caused by ion implantation.

For example, U.S. Pat. No. 4,579,463 granted to Rosencwaig et al. (that is incorporated herein by reference in its entirety) describes a method for measuring a change in reflectance caused by a periodic change in temperature of a wafer's surface (see column 1, lines 7–16). Specifically, the method uses "thermal waves [that] are created by generating a periodic localized heating at a spot on the surface of a sample" (column 3, lines 54–56) with "a radiation probe beam . . . directed on a portion of the periodically heated area on the sample surface," and the method "measur[es] the intensity variations of the reflected radiation probe beam resulting from the periodic heating" (column 3, lines 52–66).

As another example, U.S. Pat. No. 4,854,710 to Opsal et al. (also incorporated herein by reference in its entirety) describes a method wherein "the density variations of a diffusing electron-hole plasma are monitored to yield information about features in a semiconductor" (column 1, lines 61–63). Specifically, Opsal et al. state that "changes in the index of refraction, due to the variations in plasma density, can be detected by reflecting a probe beam off the surface of the sample within the area which has been excited" (column 2, lines 23–31) as described in "Picosecond Ellipsometry of Transient Electron-Hole Plasmas in Germanium," by D. H. Auston et al., Physical Review Letters, Vol. 32, No. 20, May 20, 1974. Opsal et al. further state (in column 5, lines 25–31 of U.S. Pat. No. 4.854,710): "The radiation probe will undergo changes in both intensity and phase. In the preferred embodiment, the changes in intensity, caused by changes in reflectivity of the sample, are monitored using a photodetector. It is possible to detect changes in phase through interferometric techniques or by monitoring the periodic angular deflections of the probe bean."

A brochure entitled "TP-500: The next generation ion implant monitor"dated April, 1996 published by Therma-Wave, Inc., 1250 Reliance Way, Fremont, Calif. 94539, describes a measurement device TP-500 that requires "no post-implant processing" (column 1, lines 6–7, page 2) and that "measures lattice damage"(column 2, line 32, page 2). The TP-500 includes "[t]wo low-power lasers [that] provide a modulated reflectance signal that measures the subsurface damage to the silicon lattice created by implantation. As the dose increases, so does the damage and the strength of the TW signal. This non-contact technique has no harmful effect on prod action wafers" (columns 1 and 2 on page 2). According to the brochure, TP-500 can also be used after annealing, specifically to "optimize . . . system for annealing uniformity and assure good repeatability" (see bottom of column 2, on page 4).

SUMMARY

An apparatus and method in accordance with the invention stimulate a region of a semiconductor wafer (also called "semiconductor substrate") that originally has a first number of charge carriers, so that there are a second number of charge carriers during the stimulation. The stimulation can be accomplished in any number of ways, including e.g. by use of a beam of electromagnetic radiation or by a beam of electrons. The apparatus and method use a measurement device (such as an interferometer in one embodiment) to obtain a measured value of a signal that is affected by the stimulation. In one embodiment, the affected signal is a probe beam that is reflected by the charge carriers, although other signals can be used in other embodiments.

The apparatus and method also operate a simulator (e.g. a personal computer programmed with simulation software) to generate a simulated value for the measured signal. The simulated value is based on: (i) conditions present during stimulation (as described above) and (ii) a predetermined profile of the concentration of active dopants in the region under stimulation. If the measured value matches the simulated value, then the predetermined profile used in simulation is used as a measure of the profile of active dopants in the region. The simulation my be repeated with a number of such predetermined profiles.

In one implementation, the simulations are repeated (prior to the stimulation) to obtain a set of such profiles, and the corresponding simulated values are used later to obtain a measure of the profile of active dopants in the region, e.g. by finding the closest simulated value to the measured value. In another implementation, one or more simulations are repeated after the stimulation only in case there is no match, until the simulated value and the measured value differ by less than a predetermined amount (e.g. less than 1%), and the corresponding predetermined profile is used as a measure of the profile of active dopants in the region.

The measured profile of active dopants can be used in a number of ways. In one embodiment, the measured profile is used to determine junction depth that is compared wits specifications for acceptability of the wafer. If the junction depth falls within the specifications, the wafer is processed further (e.g. in a wafer processing unit to form another layer on the substrate, or in an annealer for heat treatment of the substrate), and otherwise the substrate is identified as unacceptable and placed in a bin of rejected substrates.

In one embodiment, the apparatus and method creates charge carriers in a region of the semiconductor material (also called "carrier creation region") in a concentration that changes in a periodic manner (also called "modulation") only with respect to time. Thereafter, the apparatus and method determine the number of charge carriers created in the carrier creation region by (1) measuring an interference signal obtained by interference between a reference beam and a portion of a probe beam that is reflected by the charge carriers, and (2) comparing the measurement with predetermined data (e.g. in a graph of such measurements plotted against junction depth).

Charge carriers that are created as described above (also called "excess carriers") are in excess of a number of charge carriers (also called "background carriers") that are normally present in the semiconductor material in the absence of illumination. The concentration of excess carriers is modulated in time at a frequency that is maintained sufficiently small to ensure that the variation in concentration is aperiodic (i.e. not oscillatory, e.g. decays exponentially or according to a monotonic function). Specifically, a profile of excess carrier concentration that is devoid of a wave (along radial distance) is created as described herein when at least a majority (i.e. greater than 50%) of the charge carriers that move out of the carrier creation region do so due to diffusion.

Such a temporal modulation under diffusive conditions (also called "diffusive modulation") is used to measure an interference signal, (for example, the phase and amplitude are both measured). The measurement is used to determine (e.g. by looking up a graph or a table) one or more properties (also called "semiconductor properties") of the semiconductor material (such as junction depth). The concentration of excess carriers as a function of depth from the front surface of the semiconductor material, when measured as described herein, can also be used to determine the concentration of active dopants in the semiconductor material. Specifically, a profile of excess carrier concentration in depth is a function of the depth profile of the electric field that results from the active dopants (that form the doped semiconductor material).

An increase in excess carriers as a function of depth causes a corresponding increase in an index of refraction of the semiconductor material. Therefore, a laser beam (called "probe beam") shone on the semiconductor material is reflected back (by both background carriers and by excess carriers, but only the reflection by the excess carriers varies periodically at the modulation frequency), and a signal at the modulation frequency generated by interference between the reflected portion and a reference beam is measured as described herein. Various properties of the interference signal (such as amplitude and phase) are functions of the depth at which the reflection occurs, and can be measured to determine the depth of the junction. Note that as used herein, a junction is the boundary of any doped region (irrespective of whether the doping is a p-type dopant into an n-type substrate, a p-type dopant into a p-type substrate, or vice-versa).

A first embodiment (also called "front surface embodiment") measures the intensity of an interference signal that is obtained by interfering the reflected portion of the probe beam with a reference beam formed by another portion of the probe beam (this portion hereinafter being called "front surface beam") that is reflected by the front surface. In one variant of the front surface embodiment, a laser is used to generate another beam (called "generation beam") that is used to generate the excess carriers. The generation beam's intensity is modulated at a fixed frequency that is sufficiently low to ensure that the phase of the variation of the concentration of excess carriers is the same as (e.g. to within 10%) the phase of the generation beam over a diffusion length (wherein diffusion length is the length over which the excess charge carrier concentration decays to 1/e). Therefore, the excess carrier concentration changes approximately synchronously with the change in intensity of the generation beam. This condition ensures that the excess carrier distribution is primarily due to diffusion that can be modeled by a non-wave solution (rather than by a wave solution).

In this variant, an interferometer measures the amplitude and phase of such an interference signal, as a function of the generation beam's power and modulation, and these measurements are used to determine the concentration of excess carriers. Variation in time of the excess carrier concentration as described above allows the interferometer to use a lock-in amplifier to measure the reflected portion of the probe beam with an accuracy not possible when the excess carrier concentration is fixed.

In one implementation, a number of graphs relating the interference signal measurement to the junction depth and to the power of generation beam are determined (either by simulation or empirically). Thereafter, for a given wafer (also called "production wafer"), measurements (also called "interference measurements") of the interference signal for different powers of the generation beam are performed, and the results are compared to one or more of the just-described graphs, thereby to determine a graph that indicates the junction depth. Specifically, predetermined graphs are generated in the following manner for a number of dopant profiles that approximate an expected dopant profile of the production wafer.

Any method or device can be used to generate dopant profiles that are provided as input to a simulator (that may be a programmed computer executing a simulation program) for generation of the predetermined graphs. For example, spreading resistance profiles can be obtained on wafers (also called "reference wafers") that have been processed under known conditions and have known properties. Alternatively, dopant profiles can be simulated using commercially available simulators (that assume movement of charge carriers from the carrier creation region by diffusion).

Next, for a given dopant profile, a profile of the excess carrier concentration as a function of depth is determined using a simulator, for each of a number of powers of the generation beam. Next, a derivative of excess carrier profile as a function of depth z from the front surface is multiplied by cos(2 knz), wherein k=2π/λ, with λ being the wavelength of the probe beam, and n being the index of refraction of silicon. The product of multiplication is integrated with respect to depth and multiplied by one or more constant factors (that are related to known physical constants and to calibration of the measurement system) to determine a simulated value of the interference measurement. The simulated value of the interference measurement is thereafter plotted on a graph as a function of depth z for a selected generation beam power. The just-described acts are repeated to obtain graphs for other fixed values (e.g. two additional values) of the generation beam power. Additional such graphs are generated for different dopant profiles.

After such graphs are available, interference measurements on a production wafer at the selected generation beam power are used to look up the graphs to determine junction depth. The look up can be repeated for different interference measurements obtained by using different powers of the generation beam, to eliminate ambiguity that may result from two wafers having different junction depths but same measurements (as may occur, e.g. when changes in the two numbers being multiplied, namely (1) the derivative and (2) the cosine function (as described above) compensate for each other in the two wafers). A predetermined dopant profile having the same junction depth as that obtained by look up is thereafter used as the profile of active dopants present in the production wafer.

Measurement of the phase and amplitude of an interference signal as described herein is a significant aspect of one implementation. One or more such measurements provide a measure of a property of the semiconductor material (or a process condition) during wafer fabrication. In another implementation (also called "scanning implementation"), a number of such measurements are performed at different locations on a wafer (while the generation beam's power is maintained constant). Any change in such measurements indicates a corresponding change in the concentration of active dopants (at a predetermined depth from the front surface). Therefore, such interference measurements (from which active dopant profile is determined) are preferably (but not necessarily) monitored in one variant of the invention during wafer fabrication, to control a process step (e.g. to control annealing temperature of a wafer that has been ion implanted) used in fabricating the wafer.

When the junction depth and junction profile are measured directly on the wafer undergoing fabrication (also called "patterned wafer" or "annealed wafer"depending on the stage of fabrication), a measurement as described herein increases yield, as compared to an off-line measurement of a test wafer's properties. Moreover, such a measurement avoids the prior art cost of the test wafer itself. Such measurements are performed in one embodiment after annealing a production wafer to activate the dopants, thereby to obtain a measure that is more indicative of the electrical behavior of the devices being fabricated than a property that is measured prior to annealing (as described in U.S. Pat. No. 4,854,710).

In a second embodiment (also called "phase embodiment"), instead of the above-described interference signal, another interference signal is generated by interference between the reflected portion of the probe beam (described above) and another reference beam (hereinafter "variable phase beam") having a phase that can be changed independent of the phase of the probe beam. A phase difference (detected using, e.g. a phase detector) between two interference signals indicates the junction depth, wherein a first interference signal is obtained by interference of (1) the variable phase beam and (2) the front surface beam that is described above as the portion of probe beam reflected by the front surface, and a second interference signal is obtained by interference of (1) the variable phase beam and (2) the reflected portion of the probe beam.

In the second embodiment, the probe beam is coherent (i.e. of single chrominance, e.g. single wavelength) in addition to being polarized, so that interference with the variable phase beam can happen. Use of a reference beam in the second embodiment that is independent of the probe beam provides an increase in sensitivity of the measurement of material properties over the first embodiment, because of increased sensitivity of a phase detector used in the second embodiment to measure the interference signal. Use of an independent reference beam also allows absolute measurement of the junction depth as a fraction of the wavelength in the semiconductor.

BRIEF DESCRIPTION OF THE DRAWINGS

FIG. 9A illustrates, in a graph, the calculated excess carrier concentration per cm$^3$ as a function of depth in microns for various values of carrier lifetime within an ion implanted layer approximately 0.08 microns thick.

FIG. 9B illustrates, in a graph, the measured lock-in signal values as a function of implant dose for a variety of ion implants listed in the key in FIG. 9C. In each case the set of three points indicates the signal for implant at nominal doses of $2.5 \times 10^{11}$, $5 \times 10^{11}$, and $1 \times 10^{12}$ ions/cm$^2$, and implants representing doses ±5% above and below the nominal values.

FIG. 9C illustrates a key for the graph illustrated in FIG. 9B.

DETAILED DESCRIPTION

Figure 1A:
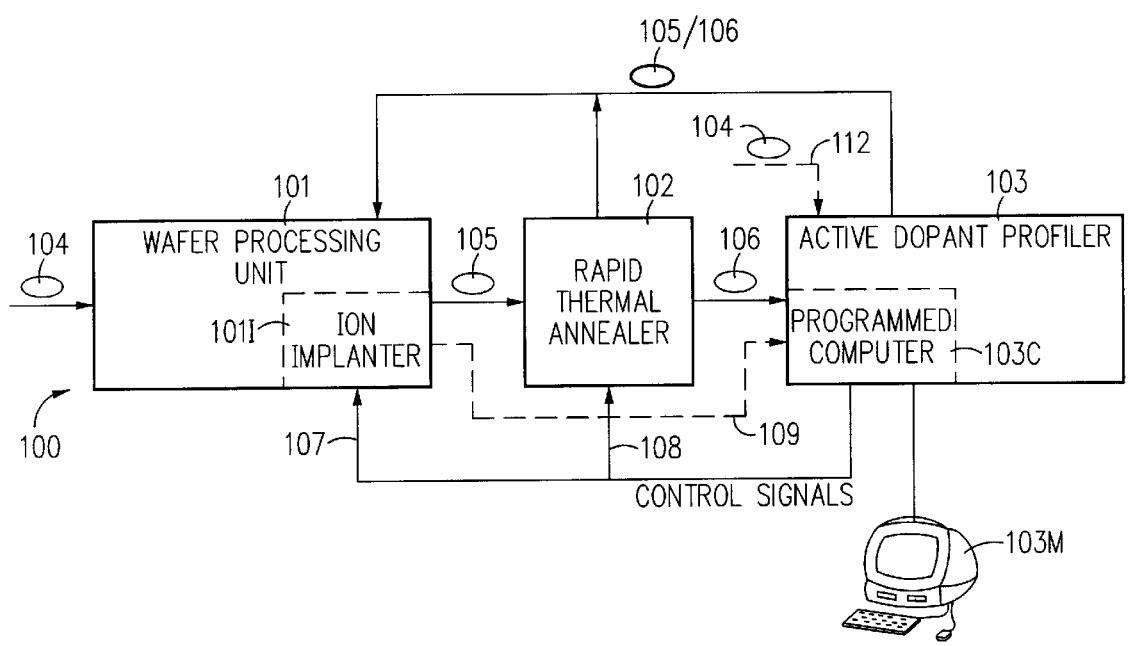
FIG. 1A illustrates, in a high level block diagram, a system including an apparatus (called "active dopant profiler") in accordance with the invention.

A wafer fabrication system 100 (FIG. 1A) in accordance with the invention is used to create integrated circuit (abbreviated as "IC") dice by processing a wafer (also called "semiconductor substrate") to form a "patterned wafer", measuring a material property of the patterned wafer, and adjusting the processing in real time if necessary. The just-described processing can include annealing, and the measurement of a material property can be performed on a patterned wafer after annealing, thereby to determine process conditions not obtainable by prior art methods, e.g. to determine anneal temperature from measurements on the annealed wafer.

Measurement on patterned wafers during fabrication as described herein eliminates test wafers that may be otherwise required in the prior art solely to monitor the fabrication process, thus reducing costs. Moreover, measurement on annealed wafers as described herein provides a measure of one or more properties that are related to the electrical characteristics (such as processing speed) of the devices being fabricated, because annealing results in activation of the dopants used in the devices.

System 100 includes an active dopant profiler (also called simply "profiler") 103 that measures various material properties in a non destructive manner. Profiler 103 includes a computer 103C that is programmed with simulation software to generate predetermined data (see operation 110 in FIG. 1B). In one implementation, operation 110 includes an act 111 wherein computer 103C generates a simulated value that is based on: (i) conditions present during stimulation, and (ii) a predetermined profile of the concentration of active dopants in the region under stimulation. Thereafter, in act 112, computer 103C checks if all predetermined profiles in a set of profiles that the wafer is likely to have been used in act 111. If not, computer 103C goes to act 113 to change the predetermined profile being used, and returns to act 111. If all profiles have been used, operation 110 is completed.

Wafer processing unit 101 and rapid thermal annealer 102 perform an operation 125 to prepare a semiconductor wafer, e.g. by forming one or more layers of the wafer (e.g. one of wafers 104–106). Thereafter, profiler 103 stimulates (see operation 126 in FIG. 1B) a region in the wafer that originally has a first number of charge carriers, so that there are a second number of charge carriers during the stimulation (see operation 126 in FIG. 1B). The stimulation can be accomplished in any number of ways, including e.g. by use of a beam of electromagnetic radiation or by a beam of electrons.

Next, in operation 140, profiler 103 measures a property of the region that is affected by the stimulation. In one implementation, profiler 103 uses (see act 141) a measurement device (such as an interferometer in one embodiment) to obtain one or more measured values (e.g. amplitude and phase) of a signal (such as a probe beam that is reflected by the charge carriers) that is affected by the stimulation. Next, profiler 103 compares (see act 142) the measured values with one or more of the simulated values (generated in operation 110) to identify the simulated value that is closest to the measured value. Thereafter, profiler 103 uses the predetermined profile that was used to generate the closest simulated value as the profile in the wafer. For example, profiler 103 determines a value of a semiconductor property (such as "junction depth") in the region, based on the profile used to generate the closest simulated value. Profiler 103 can determine the value in any number of ways, e.g. by computation or by looking up a table or a graph that relates each profile to a corresponding value of the semiconductor property.

Next, in act 160, profiler 103 checks if the property value matches the specifications for acceptance of the wafer. If so, profiler 103 simply returns to operation 125. and otherwise goes to act 161. In act 161 profiler adjusts one or more process conditions present during preparation of the wafer, e.g by driving a control signal on one or more of lines 108 and 107 to annealer 102 and wafer processing unit 101. Thereafter, profiler 103 returns to operation 125.

Figure 1B:
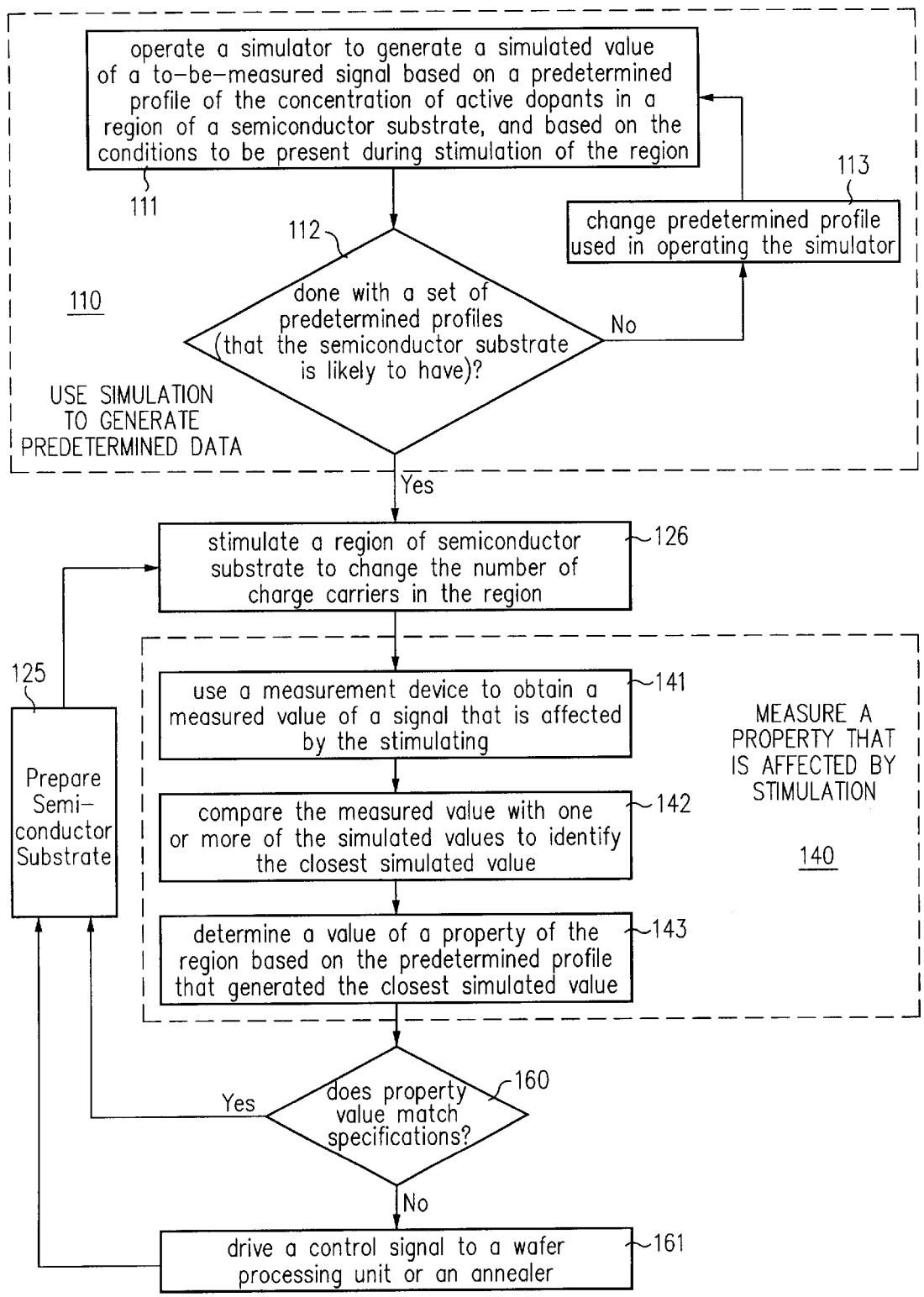
FIGS. 1B and 1C illustrate, in high level flow charts, a method performed by the apparatus of FIG. 1A.
Figure 1C:
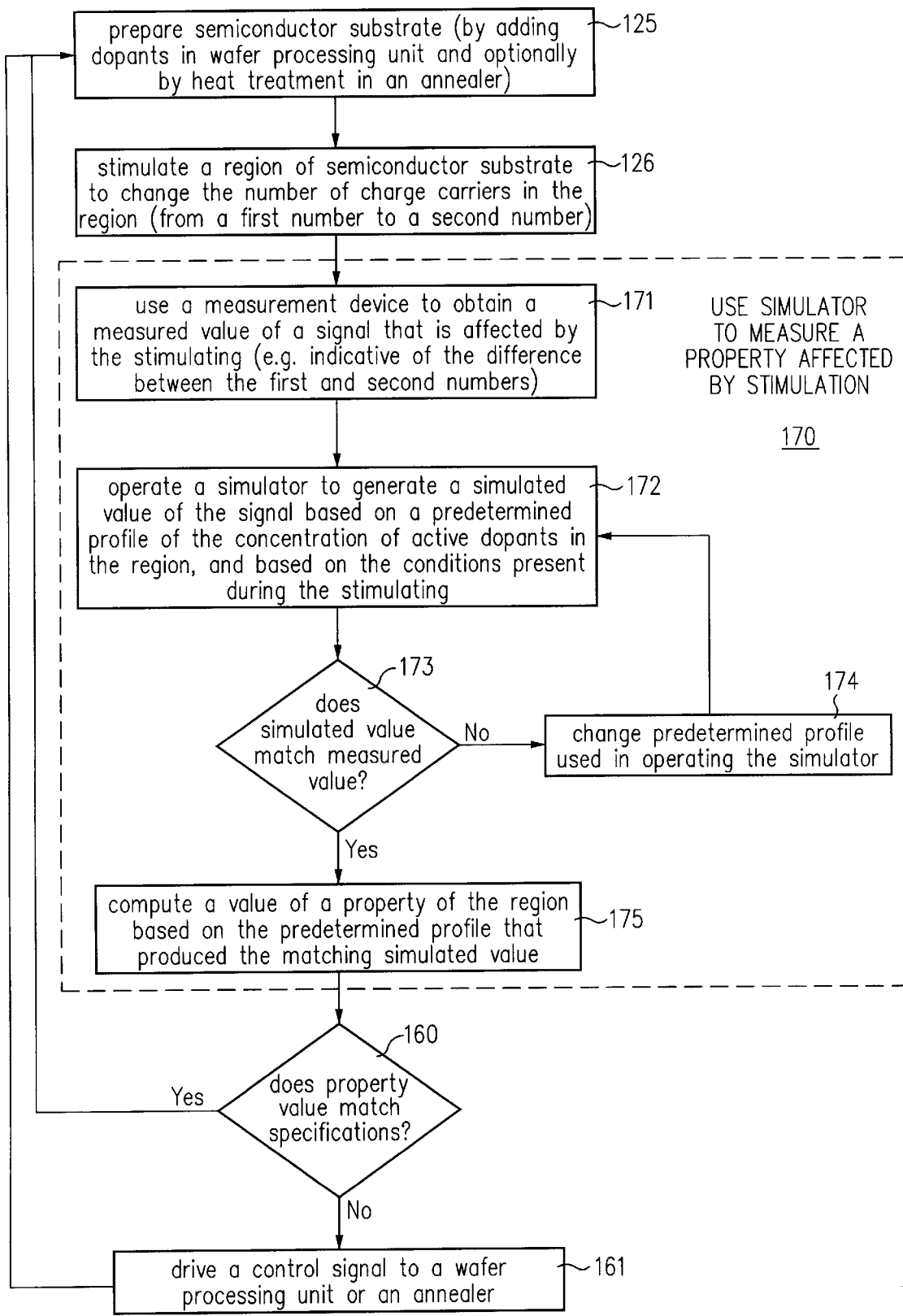

Although in one implementation (described above in reference to acts 111–113, the simulations are repeated for a set of profiles prior to the stimulation, in another implementation illustrated in FIG. 1C, one or more simulations are repeated after the stimulation. For example, wafer processing unit 101 and rapid thermal annealer 102 perform operation 120, and profiler 103 performs operation 126 (as described above in reference to FIG. 1B) and thereafter performs operation 170. In operation 170, profiler 103 uses a measurement device to obtain a measured value (as described above in reference to act 141) and thereafter goes to act 172. In act 172, profiler 103 operates a simulator to generate a simulated value of the signal based on a predetermined profile (as described above in reference to act 111). Next, in act 173, profiler 103 checks if the simulated value matches the measured value (e.g. within a predetermined percentage, such as 1%). If there is no match, profiler 103 goes to act 174 and changes the predetermined profile that was used in operating the simulator (in act 172), and returns to act 172. If there is a match, profiler 103 goes to act 175 to determine the semiconductor property's value (as described above in reference to act 143). Next, profiler 103 performs acts 160 and 161 as described above in reference to FIG. 1B.

In one embodiment, profiler 103 implements the stimulation operation by creating a number of charge carriers in a to-be-tested wafer. The charge carriers created by profiler 103 are in excess of a number of charge carriers (also called "background carriers") that are normally present in a semiconductor material (e.g. due to dopants that are defined to be atoms that occupy sites in the crystal lattice of the semiconductor material, and thus contribute to the electrical conductivity of the material) in the absence of illumination.

The excess carriers, when produced in one embodiment, distribute themselves in semiconductor material 156 (FIG. 1E) in a profile 158 (see FIG. 1D; defined to be the concentration in number of carriers per cubic cm) that exceeds the level of carriers present without stimulation (such as illumination) formed within material 156 by the dopant atoms. Specifically, the excess carrier concentration $n_e$ changes from being zero outside a front surface 153 (FIG. 1E) of the semiconductor material 156 to a finite value inside the semiconductor material 156 (thereby resulting in a step increase in the concentration at front surface 153).

As the depth z from front surface 153 (FIG. 1E) increases, the excess carrier concentration $n_e$ increases over a depth (e.g. less than 200 Å) that is at least an order of magnitude smaller than the wavelength (e.g. 4000 Å) of probe beam 152 within material 153 (that is the free space wavelength/refractive index). Beyond the just-described depth, excess carrier concentration $n_e$ changes further in a manner proportional to a change in the concentration of dopant atoms until depth z reaches the edge of the doped region, at a junction depth Zj. For example, in some cases, the dopant concentration rises, but in other cases the dopant concentration dips first and then rises, depending on the detailed shape of the doping profile.

Beyond junction depth Zj, the excess carrier concentration $n_e$ returns to being substantially constant to a depth on the order of 10 times the depth of the doped region (i.e. varies less than 10%, especially for shallow doped regions less than or on the order of 0.1 microns deep). The above-described profile, when produced as described herein, varies periodically with time, in synchronization with the modulation frequency, but does not vary periodically in space, as a function of radial distance r (FIG. 1D). Instead, concentration $n_e$ simply decays radially (e.g. monotonically as a function of radial distance r) outside region 120, as illustrated in FIG 1D. Specifically, over a time period that is the inverse of the modulation frequency, profiler 103 changes concentration $n_e$ between the values $n_{ea}$–$n_{en}$, wherein $n_{en} \leq n_{ej} \leq n_{ei} < n_{ea}$ (FIG. 1D).

Therefore, at any given time ti, the value $n_{ei}$ of the carrier concentration in semiconductor material 156 decays as a function of radial distance r, without the creation of a wave in space (outside region 120). A profile of excess carrier concentration $n_e$ that is devoid of a wave (along radial distance r) is created as described herein when at least a majority (i.e. greater than 50%) of the charge carriers (defined to be both excess carriers and background carriers) that move out of region 120 do so due to diffusion. Within illuminated region 120 the carrier concentration may show spatial variation due to (1) variations in the profile of the generation laser beam (typically a smaller effect) and (2) doping profile variations.

Such a "diffusive modulation" of excess charge carriers is a significant aspect of the invention because the predetermined data used in looking up the semiconductor properties are based on a diffusive solution of an equation 15 (described below) for the movement of charge carriers from region 120 (also called "carrier creation region"). Superposition of a wave solution (on the diffusive solution) degrades the accuracy of the predetermined data, because the wave solution perturbs the excess carrier profile away from the aperiodic profile assumed for the diffusive solution.

In one embodiment, generation beam 151's intensity is modulated at a fixed frequency that is sufficiently low to ensure that the phase of the variation of concentration $n_e$ is the same as (e.g. to within 10%) the phase of generation beam 151 over a diffusion length (wherein diffusion length is the length over which a charge carrier decays to a value of 1/e). Therefore, concentration $n_e$ changes approximately synchronously with the change in intensity of generation beam 151. This condition. ensures that the excess carrier distribution is primarily due to diffusion that can be modeled by a non-wave solution (rather than by a wave solution).

To ensure the absence of a wave in space, the frequency of modulation of concentration $n_e$ is selected to be several times (e.g. one or more orders of magnitude) smaller than the modulation frequencies used in the prior art to generate waves as described in, for example, U.S. Pat. No. 4,854,710. Specifically, in one implementation of this invention, the modulation frequency is approximately 1 KHz that is one thousand times (three orders of magnitude) smaller than a 1 MHz frequency described in column 15, line 18 of U.S. Pat. No. 4,854,710 by Opsal. Use of such a low modulation frequency is a critical aspect in one embodiment of profiler 103 (FIG. 1A), and leads to unexpected results due to the elimination of a wave in space, such as the "wave" described by Opsal.

An alternative embodiment of profiler 103 modulates a generation beam at a frequency that is higher than the above-discussed frequency. Specifically, the alternative embodiment causes periodicity in space outside of region 120. However, in the alternative embodiment, the wavelength of the spatial periodicity is selected to be greater than ten times the diffusion length, so that within region 120 the effects of spatial periodicity are negligible.

An increase in concentration $n_e$ (as illustrated by profile 164 in FIG. 1G) that occurs when the distribution of excess carriers forms in region 120 in response to generation beam 151, results in a proportional increase in the index of refraction "n" of the semiconductor material 156. An index of refraction gradient with respect to depth is thereby formed in region 120. Because of the linear proportionality; between excess carrier concentration and the index of refraction, profile 164 also represents the index of refraction as a function of depth.

Specifically, excess carrier profile 164 (FIG. 1G) may be modeled as a set of thin layers of excess carriers, such as layers 164A–164T $A \leq J \leq T$, T being the total number of layers, wherein each layer 164J has a constant carrier concentration. The index of refraction of silicon is a function of the carrier concentration, so each layer 164J has a slightly different index of refraction. Consequently, a small amount of energy of probe beam 152 reflects from each interface 165J between layers 164J and 164J+1, with the amount of reflection being proportional to the carrier concentration in layer 164J that is located above interface 165J.

The sum of all such reflections within region 130 (that has the graded index of refraction) forms a component 163 that is smaller than another component 162 of the reflection of beam 152. Specifically, component 162 is a reflection of beam 152 from front surface 153, and is the sum of three subcomponents: (1) the first is due to the discontinuity between air and silicon. (2) the second is due to the sudden rise in doping profile at the surface. (3) the third is due to the sudden rise in the excess carrier concentration at the surface. The strongest subcomponent of reflection 162 from front surface 153 is the first, by several orders of magnitude as compared to the second and the third.

Note that component 163 has a phase that is delayed with respect to component 162, because light reflected from the index gradient region 130 propagates an additional distance Zj into the semiconductor and back out. Therefore, component 162 interferes with component 163, and the interference may be constructive, destructive, or a combination of both, depending upon the range of depths Zj over which the index gradient occurs. Thus, a signal obtained by summing the reflection component 162 (from front surface 153), and the reflection component 163 (from graded index region 130) contains within its amplitude and phase, information about the depth and shape of profile 164 of the excess carrier concentration.

System 100 includes a wafer processing unit 101 that performs one or more initial activities in act 201 (e.g. receiving wafers), and thereafter goes to operation 210 (FIG. 2A) that is similar or identical to operation 110 (described above). Next (or immediately after act 201), the apparatus prepares the semiconductor wafer (in operation 220). In operation 220, unit 101 performs an act 221 to form doped regions, e.g. by operating an ion implanter 1011 to create, in a wafer 104 (FIG. 1A), one or more regions (e.g. doped region 130 in FIG. 1C) that have dopant atoms (e.g. boron atoms in silicon). Instead of ion implantation, any other process for creating doped regions, e.g. chemical vapor deposition, epitaxial deposition, evaporation, diffusion, or plasma deposition can be used in unit 101 (FIG. 1A) to perform act 202.

Figure 2A:
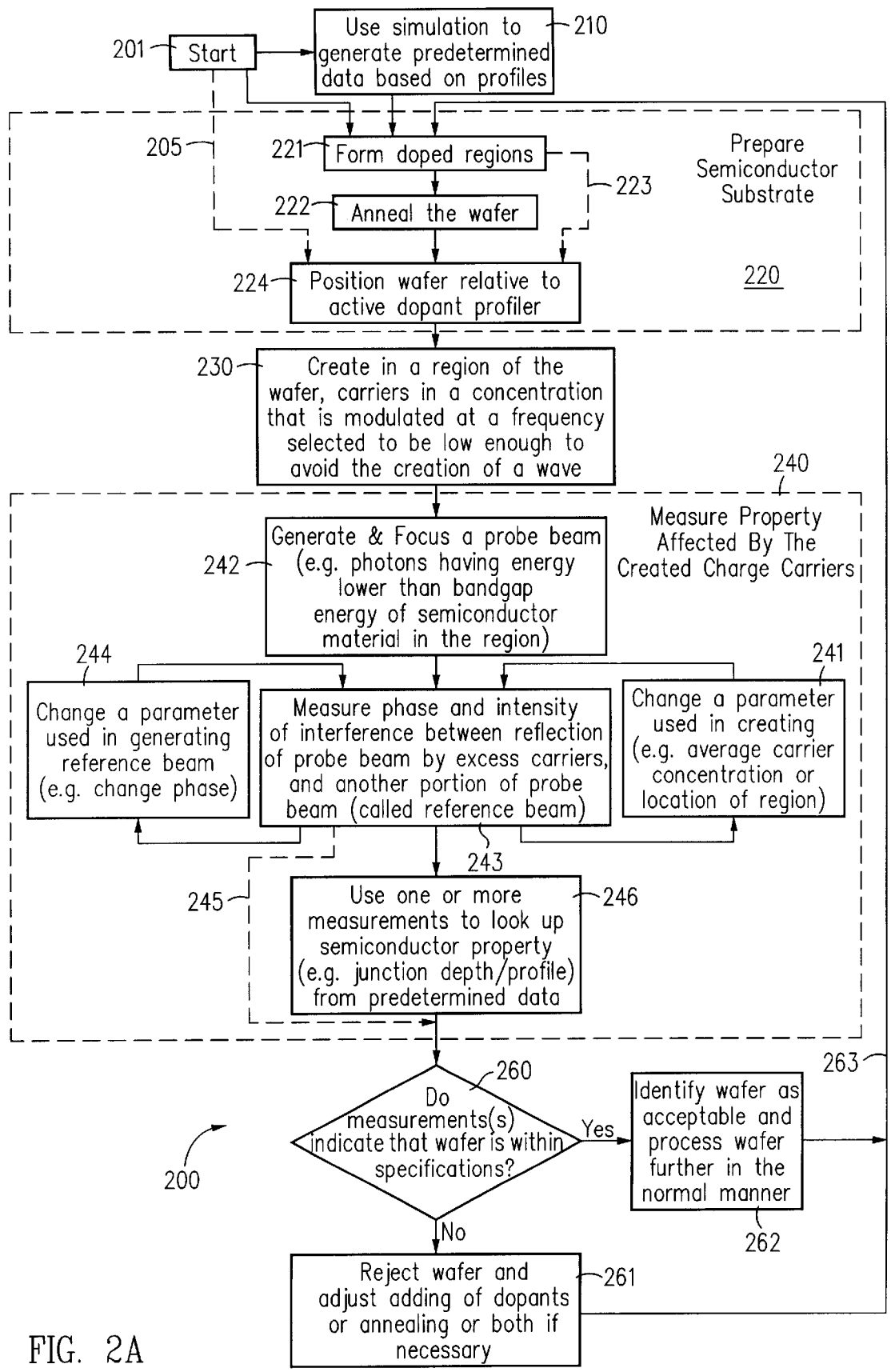
FIG 2A illustrates, in a flowchart, the acts performed by the profiler of FIG. 1A in one implementation.

Thereafter, a patterned wafer 105 having one or more patterns of doped regions is transferred to a rapid thermal annealer 102 (FIG. 1A) that may be included in system 100. Rapid thermal annealer (also called "annealer") 102 performs an annealing act 222 (FIG. 2A), e.g. by heating wafer 105 (FIG. 1A) to a predetermined temperature (also called "annealing temperature"), e.g. to remove damage that is normally caused by ion implanter 101 to the lattice structure of the semiconductor material in the doped regions of wafer 105. Instead of a rapid thermal annealer, a furnace may be included in system 100 and used to anneal wafer 105 in act 222 (FIG. 2A).

Anneals (as illustrated in act 222) are typically done by heating the wafer rapidly with lamps (not shown) in annealer 102 (FIG. 1A). The illumination by the lamps in annealer 102 may not be uniform, and the amount of heat that enters a patterned wafer 105 at any point may be a function of the thickness of dielectric layers (such as silicon dioxide or silicon nitride to be formed on surface 153), and the integrated circuit pattern therein. Specifically, the different layers (not shown) of doped region's in wafer 105 reflect different amounts of power, thereby causing variations in the amount of heating of wafer 105. Thus annealing of implanted wafer 105 may not be uniform, and the characteristics of a junction (formed at an interface between doped region 130 and semiconductor material 156 in FIG. 1E at a depth Zj from surface 153) in annealed wafer 106 may vary from point-to-point.

Annealing in act 222 causes the dopant atoms (also called "dopants") to move into the lattice of the semiconductor material in a doped region 130, where the dopants act as donors (forming n-type material) or acceptors (forming p-type material). The extent to which the dopants incorporate into the lattice structure during act 222 is a function of the temperature at which and the time for which act 222 is performed. The incorporation is more complete at a higher temperature or after a longer time.

However, the dopants also diffuse (i.e. move) during act 222, thereby increasing the junction depth. The diffusion proceeds more rapidly at a higher temperature, and it is necessary to carefully control the annealing temperature. Therefore, a junction depth or profile of the concentration of dopants as a function of depth is measured after act 222, and the measurement is compared with predetermined information (e.g. a specification or information obtained from profiles/junction depths of wafers known to be good) to determine a change (if any) to be mad;e to the annealing process. Dynamic feedback of such to-be-made changes to the annealing process in real time as described herein improves the yield of good wafers obtained from annealing in a manner not otherwise possible in the prior art.

After annealing, wafer 106 (FIG. 1A) is transferred from rapid thermal annealer 102 to profiler 103, and positioned therein (see act 224 in FIG. 2A). In an alternative embodiment, an active dopant profiler is integrated into a rapid thermal annealer and does not require positioning after completion of anneal. In one embodiment, profiler 103 is moved relative to wafer 106 instead of moving wafer 104.

Also, a non-annealed wafer 105 can be used (moved via path 109 in FIG. 1A) as illustrated by branch 223 in FIG. 2A e.g. if dopant regions do not require annealing due to use of a method other than ion implantation, such as diffusion (wherein dopants are diffused into wafer 105 thermally, and are active, and there is no need to anneal out implant damage). Profiler 103 evaluates the efficacy of the dopants in a nonannealed wafer 105 in a manner similar to that described above for annealed wafer 106.

A starting wafer 104 can also be used as illustrated by path 112 in FIG. 1A and by branch 205 in FIG. 2A. Therefore, in the following description, the notation "104/105/106" is used to indicate that the description is equally applicable to each of wafers 104, 105 and 106. Similarly the notation "105/106" indicates description applicable to each of wafers 105 and 106.

Next, after a wafer 104/105/106 is appropriately positioned (e.g. centered or aligned to a predetermined pattern located within the wafer), profiler 103 stimulates a region 120 of the wafer, e.g. by creating (see operation 230 in FIG. 2A) in a region 120 of the wafer, a number of charge carriers that are modulated at a predetermined frequency. The predetermined frequency is selected to ensure that a wave of the charge carriers is not created inside carrier creation region 120 during the act of measurement (see operation 240 in FIG. 2A). For example, the predetermined frequency may be selected to be any frequency in conformance with the formula $f \leq (1/2\pi\tau)$ where f is the frequency, and $\tau$ is the lifetime of an excess charge carrier in the substrate. As profiler 103 does not use a "plasma wave" as described in U.S. Pat. No. 4,854,710, profiler 103 is as effective in measuring a property of an annealed wafer 106 as in measuring a property of a non-annealed wafer 104/105.

Figure 4A:
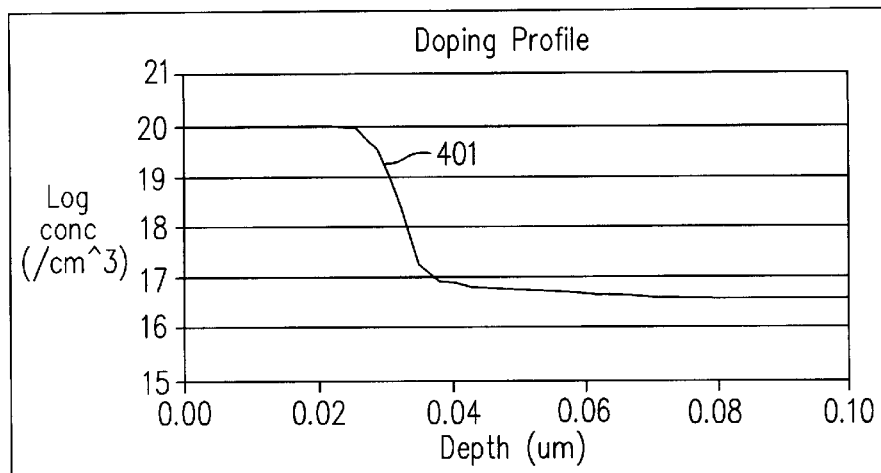
FIG. 4A illustrates, in a graph, concentration of active dopants as a function of depth from the front surface of the semiconductor material (also called "active doping profile") for use in generation of predetermined data, obtained by performance of act 211 illustrated in FIG. 2B.

Profiler, 103 (FIG. 1A) measures a property (in operation 240 in FIG. 2A) that is affected by charge carriers present in a doped region 130 (FIG. 1C) in a wafer 105/106. In one implementation, the measured property is complex reflectance (that is, reflected portion's amplitude and phase), and profiler 103 uses the measurement to determine various properties (also called "semiconductor properties") such as junction depth, and the number of active dopants as a function of depth "Z" from surface 153 of wafer 105/106. A function (called "active dopant profile") based on the measurement can be plotted in a graph as illustrated in FIG. 4A described below. In other embodiments of operation 240, instead of complex reflectance, profiler 103 can measure other properties affected by the created charge carriers such as the refractive index.

Figure 2B:
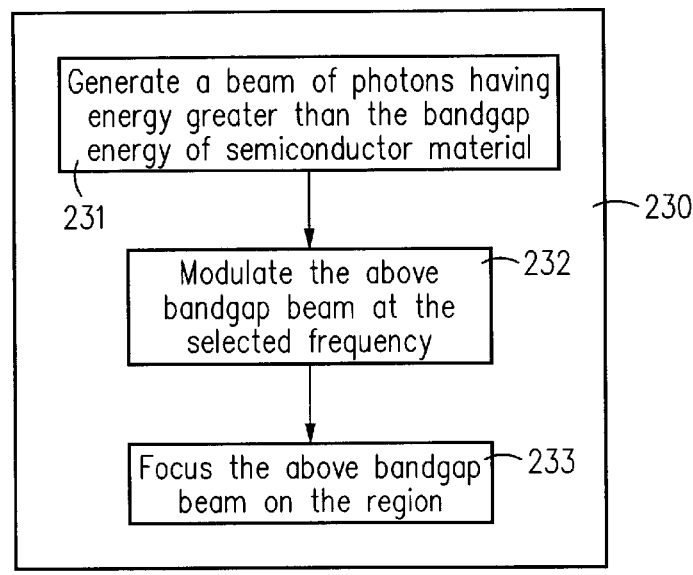
FIG. 2B illustrates, in a flow chart, creation of charge carriers in act 230 (illustrated in FIG. 2A) performed by the profiler of FIG. 1A.
Figure 2C:
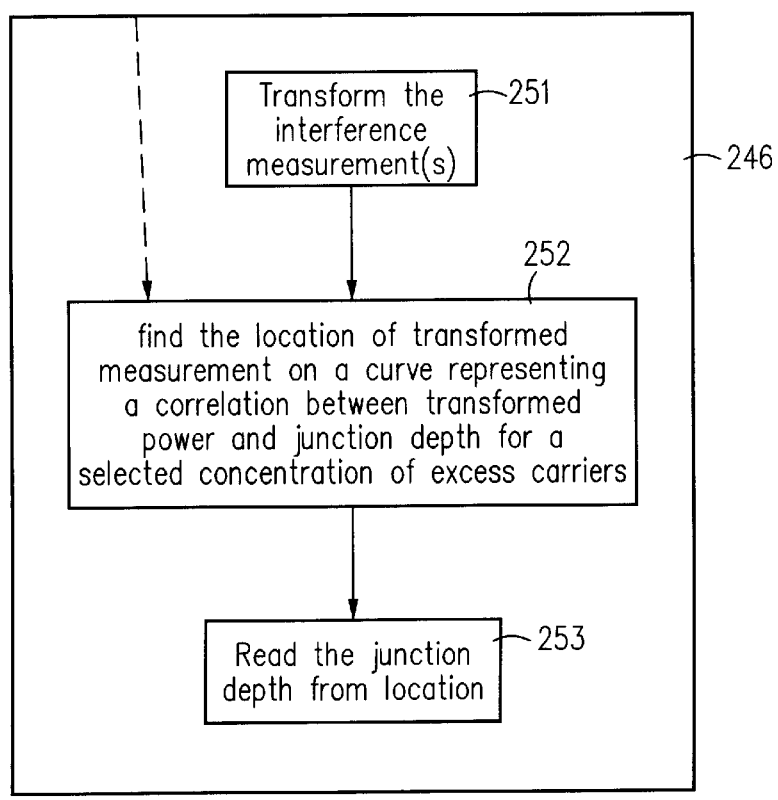
FIG. 2C illustrates, in a flow chart, use of the measurements in optional act 250 (illustrated in FIG. 2A) performed by the profiler of FIG. 1A.
Figure 2D:
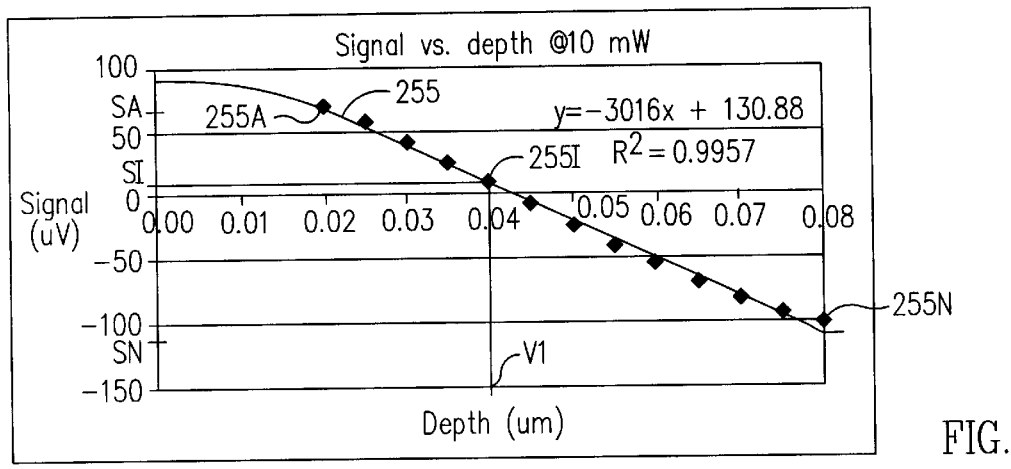
FIGS. 2D–2F illustrate various graphs containing the predetermined data that are used in one embodiment of act 210 illustrated in FIG. 2A.

One or more of these measurements can be used (see act 246 in FIG. 2A) to lookup a material property from predetermined information (also called "predetermined data") as described below in reference to FIG. 2C. Act 246 is an optional act, and is performed in one embodiment only after performance of another optional operation 210, for generation of predetermined data (either empirically or by simulation or some combination thereof) in the form of measurements for wafers known to be good (i.e. expected measurements for wafers that fall within predetermined specifications for acceptance of wafers). Operation 210 is described below in detail in reference to FIGS. 2D–2F.

One or more of these measurements may also be used (see act 260 in FIG. 2A) by comparison against one or more predetermined limit(s) to determine if annealed wafer 106 conforms to the specification for such wafers. If wafer 106 conforms to the specifications, wafer 106 is identified (in act 262) as being acceptable (e.g. by movement in the direction for further processing) and the conditions in wafer processing unit 101 (FIG. 1A) and in rapid thermal annealer 102 are left undisturbed. Thereafter, the above-described acts are repeated (as illustrated by branch 263) on another wafer or after further processing on the same wafer.

If a wafer 106 does not conform to the specifications, wafer 106 is identified (in act 261) as unacceptable (e.g. discarded) and optionally profiler 103 adjusts (either automatically or under manual control) (1) the conditions (e.g. dosage of dopants) in unit 101 by driving a signal on a line 107 (FIG. 1A), or (2) the conditions (e.g. annealing temperature) in annealer 102 by driving a signal on line 108, or both. Then the above-described acts are again repeated (as illustrated by branch 263) on another wafer 106.

As described below, the measurement performed by profiler 103 is non-destructive, is performed in a few square microns, and can be performed in a relatively short time (e.g. five seconds in one region or 50 seconds at 10 regions over a wafer). Measuring a property of annealed wafer 106 during (or immediately after) fabrication as described herein increases yield, as compared to an off-line measurement of a test wafer's properties.

Prior to measuring a material property by performing operation 240, profiler 103 creates (see act 230 in FIG. 2A), in a region 120 (also called "carrier creation region") of wafer 106, a concentration $n_e$ of excess carriers, and modulates concentration $n_e$ (i.e. increases and decreases) as a function of time t. The excess carriers can be created by any method, although in one embodiment, the excess carriers are created by a generation beam 151 that may be a beam of electromagnetic radiation. In another embodiment, the source of excess carriers is a beam of electrons.

Figure 1E:
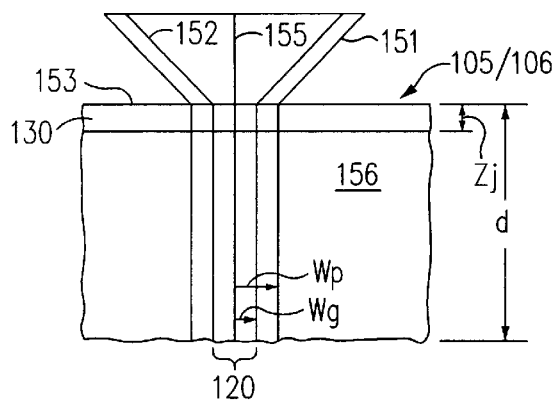
FIG. 1E illustrates, in a cross-sectional view of the semiconductor, use of a probe beam, a generation beam, and an optional reference beam used by the active dopant profiler of FIG. 1A in various embodiments described herein.
Figure 1D:
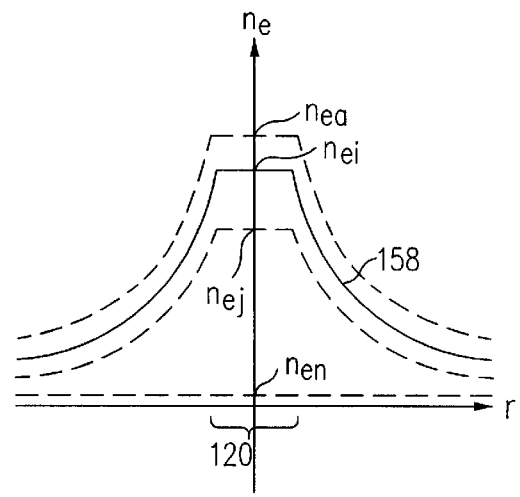
FIG. 1D illustrates, in a graph, the temporal modulation of charge carriers by one embodiment of the active dopant profiler of FIG. 1A, without creation of a wave of charge carriers.
Figure 1F:
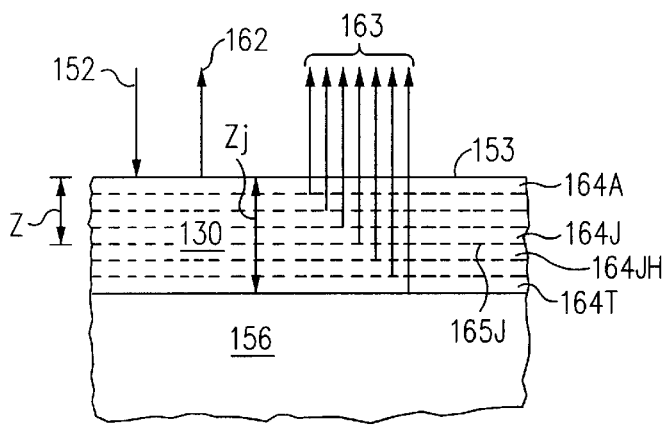
FIG. 1F illustrates, in another cross-sectional view, modeling of excess carriers in layers in the semiconductor.
Figure 1G:
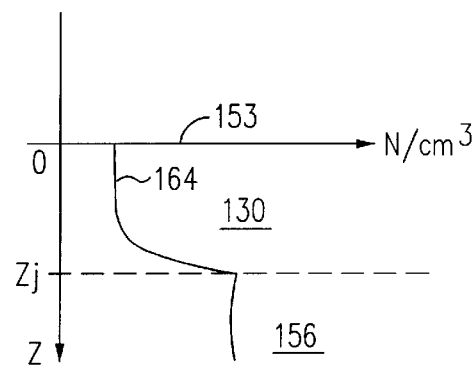
FIG. 1G illustrates, in a graph, the concentration of excess charge carriers as a function of depth Z from front surface 153.
Figure 5:
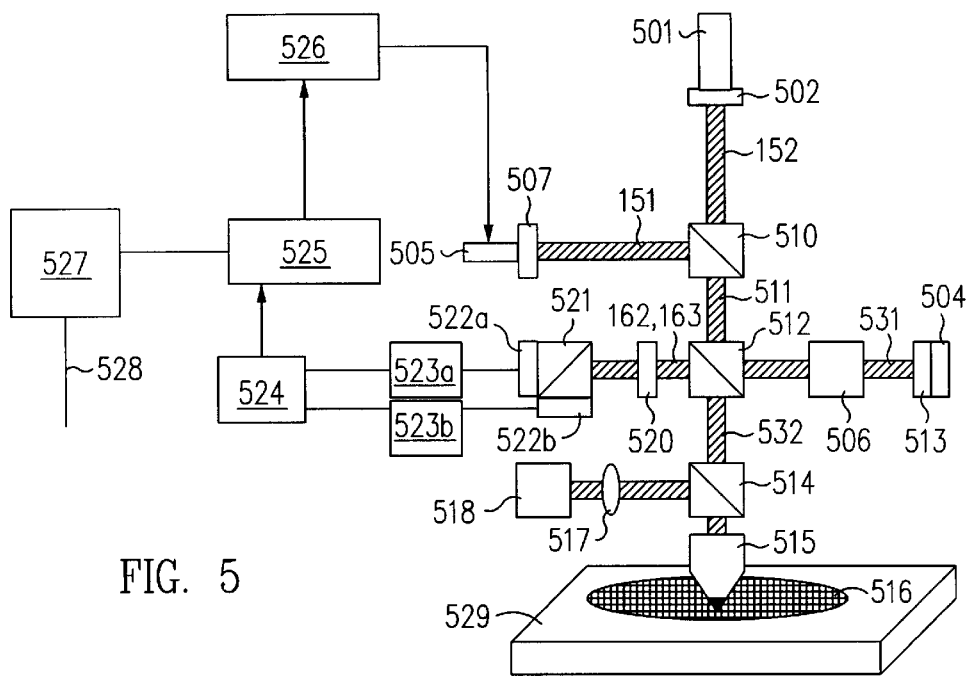
FIG. 5 illustrates, in a block diagram, various components used in one implementation of the active dopant profiler of FIG. 1A.

In one embodiment, probe beam 152 is smaller in diameter than generation beam 151 (as illustrated in FIG. 1E) due to the chromatic aberration of the focusing lens (e.g. lens 515 in FIG. 5). Moreover, probe beam 152 can have a longer wavelength than generation beam 151, to ensure that the rate (also called "generation rate") of generation of carriers due to probe beam 152 is significantly less than the generation rate due to generation beam 151. In one embodiment, generation beam 151 has a first wavelength $\lambda g$ and probe beam 152 has a second wavelength $\lambda p$, the second wavelength $\lambda p$ being determined from the formula:

$$\lambda g \geq [(10\alpha p P p \lambda p)/(\alpha g P g)][w_g/w_p]^2$$

wherein $\alpha p$ and $\alpha g$ are the absorption coefficients in semiconductor material 156 (FIG. 1C) of probe beam 152 and generation beam 151 respectively, Pp and Pg are the powers of probe beam 152 and generation beam 151 respectively, and $w_g$ and $w_p$ are the radii of the focal spots at front surface 153 of beams 152 and 151 respectively. This formula ensures that at front surface 153 the generation rate due to generation beam 151 is at least an order of magnitude greater than the generation rate due to probe beam 152.

The wavelength of probe beam 152 is typically longer than the wavelength of generation beam 151 as illustrated in FIG. 1E. Since, for a lens the focal spot size at surface 153 is proportional to the wavelength, probe beam 152 will typically focus to a larger spot size than generation beam 151. It is desirable to have the opposite relationship, in which probe beam 152 is smaller than generation beam 151 at the focus, so that probe beam 152 is positioned within generation beam 151, as shown in FIG. 1E. This makes the measurement less sensitive to the radial decay of the excess carrier concentration.

An appropriate relationship between beams 151 and 152 is achieved using the chromatic aberration of a focusing lens 515 (FIG. 5). At the focus of probe beam 152, generation beam 151 is slightly out of focus, and, hence, has a slightly larger diameter than at focus. Measurements are made with this focal arrangement, in which generation beam 151 spot is at focus, with a minimum diameter, and generation beam. 151 spot is out of focus, having a slightly larger diameter than the probe beam 152.

In one embodiment, profiler 103 implements the above-described act 230 (FIG. 2A) by: generating (act 231 in FIG. 2B) a beam 151 (FIG. 1E) of photons that have energy greater than the bandgap energy of the semiconductor material in doped region 130, modulating (act 232 in FIG. 2B) beam 151 at a frequency selected to avoid the creation of a wave (as described above), and focusing (act 233 in FIG. 2B) beam 151 on doped region 130. However, in an alternative embodiment described below in reference to measurement of the depth of an amorphous layer, profiler 103 implements the above-described act 231 (FIG. 2B) by generating a beam 151 of photons that have energy lower than the bandgap energy of the semiconductor material (amorphous silicon) in doped region 130.

Depending on the implementation, profiler 103 modulates the intensity of generation beam 151 at any frequency in the range of 1 Hz to 20,000 Hz. The modulation frequency can be, for example, 1000 Hz, and may require at least 10 cycles for a lock-in amplifier to generate a reflectance measurement (based on a probe beam as described below in reference to act 242), or 10 milliseconds to perform each reflectance measurement. In one example, the throughput is 30 wafers per hour, or 120 seconds per wafer, with each wafer having a measurement taken in at least ten regions.

If a material property measurement requires several reflectance measurements (e.g. a single region 120 requires a number of reflectance measurements for each of a corresponding number of average carrier concentrations that may be obtained at a range of powers of generation beam 151 (10 powers are linear spaced between 5 mW and 100 mW average power, for example)), profiler 103 takes several seconds (e.g. 10–100 seconds) for each wafer 104/105/106. Hence, the 10 millisecond speed of reflectance measurement per region allows for real time control in the fabrication of wafers by apparatus 100 (FIG. 1A) using method 200 (FIG. 2A).

In another implementation of act 230, instead of using beam 151 of photons, profiler 103 uses a beam of charged particles, such as electrons or ions. The beam of charged particles is modulated and focused in the same manner as that described herein in reference to beam 151 to generate the charge carriers in doped region 130. Instead of a beam of photons or a beam of electrons, any other mechanism (such as a combination of photons and electrons) can be used to create charge carriers in act 230 (FIG. 2A).

In act 240, one implementation of profiler 103 focuses (see act 242 in FIG. 2A) on a region (also called "carrier creation region") 120 illuminated by beam 151, another beam 152 (FIG. 1E) that is used to detect the number of charge carriers in wafer 104/105/106 when illuminated by beam 151. In one embodiment, beam 152 (also called "probe beam") contains photons having energy lower than the bandgap energy of the semiconductor material in carrier creation region 120. Such a probe beam 152 limits the creation of additional carriers (due to the probe beam, also called "measurement-related carriers") when beam 152 is incident on carrier creation region 120, thereby to maintain the charge carrier concentration approximately the same prior to and during measurement (see act 243 in FIG. 2A) of an interference signal as described below.

Next, profiler 103 measures (see act 243 in FIG. 2A) the amplitude and phase of a signal generated by interference between a probe beam 152 (FIG. 1E) reflected by the excess charge carriers within region 156 (FIG. 1E) and a reference beam (that may be either a portion of the probe beam reflected from front surface 153, or another portion of the probe beam that has a variable phase, the phase being varied as described below in reference to act 244). As the interference signal being measured is modulated at the frequency of modulation of the charge carriers in carrier creation region 120, a lock-in amplifier (described below) may be used to improve accuracy of the measurement.

The measurement in act 243 (FIG. 2A) provides an indication of an average concentration $n_{av}$ of charge carriers in doped region 130 near surface 153, wherein the average concentration $n_{av}$ is a root mean square average that is measured over the period of one (or more) modulation cycle(s) at the modulation frequency of generation beam 151. Concentration $n_{av}$ in turn indicates, under certain conditions as discussed below, a material property, e.g. the junction depth in doped region 130.

In one embodiment, the location at which the charge carriers are created is not changed between two or more measurements. Instead, in one implementation, profiler 103 performs a number of measurements at the same location (e.g. at least two measurements for two different powers of generation beam 151) in wafer 105/106, but changes a parameter used to create the charge carriers. The parameter can be, for example, the average carrier concentration $n_{av}$ in region 120.

Concentration $n_{av}$ is changed e.g. by changing the intensity of generation beam 151 (e.g. by changing the power or the diameter), and act 243 is repeated. Alternatively, profiler 103 can change the location of carrier creation region 120 and perform a number of such measurements. In one implementation, the locations of each of probe beam 152 and generation beam 151 are changed to obtain a linear scan across a wafer 104/105/106, while holding the beams 151 and 152 coincident each with the other. Also, instead of or in addition to act 241, profiler 103 changes a parameter used in the measurement as illustrated by act 244 in FIG. 2A, e.g. changes phase of the reference beam.

In the above-described embodiments, a probe beam 152 having photons of energy below the bandgap energy of wafer 156 is used, although in another embodiment probe beam 152 has photons of energy equal to or slightly above (e.g. 5% above) the bandgap energy. Certain additional carriers (called "measurement-related carriers") created by probe beam 152 are in a sufficiently small percentage (e.g. an order of magnitude smaller than the number created by the generating beam) to provide a reasonably accurate measurement (e.g. to within 5%). Note that the overall accuracy of a measurement as described herein is also governed by other inaccuracies involved in the act of measuring, e.g. inaccuracies in a measurement device, such as a lock-in amplifier.

Therefore, in one embodiment the inaccuracy caused by the measurement-related carriers is kept only as small as necessary to maintain the overall accuracy below a predetermined limit. Specifically, the percentage of measurement-related carriers is kept sufficiently small when the rate per unit volume of the carriers generated by generation beam 151 (obtained by dividing the photon flux per unit area by the absorption length), is at least one order of magnitude (or more) larger than for probe beam 152.

The photon flux per unit area in region 120 due to generation beam 151 is the number of photons per unit area obtained by dividing the power P of generation beam 151 by the area $(\pi W_0^2)$ of illumination, where $W_0$ is the radius of generation beam 151, by Plank's constant h and the ratio of the speed c of light to the wavelength $\lambda$ as shown in the following formula: photon flux=$(P/\pi W_0^2) \times (1/h(c/\lambda))$. The absorption length is the depth from surface 153 at which the intensity of generation beam 151 drops to (1/e) of the intensity at surface 153 (see equation 23).

In one implementation, probe beam 152 has a generation rate one or more orders of magnitude smaller than the generation rate of generation beam 151. As noted above, the difference in generation rates is obtained by using beams 151 and 152 that have different absorption lengths in the semiconductor material of wafer 156, or by generating beams 151 and 152 at different powers or different diameters, or all of the above. In various implementations, the pair of beams 151 and 152 are generated by one of the following pairs of lasers: (AlGaAs, InGaAs), (Ar, InGaAs), (Nd:YAG , InGaAs), and (Nd:YAG, AlGaAs).

In one or more of the implementations, e.g. for use of lasers (Nd:YAG, AlGaAs), the power of probe beam's laser (e.g. AlGaAs) is maintained less than the power of generation beam's laser (e.g. Nd:YAG) because the absorption length of the probe beam is a fraction (e.g. one-tenth) of the absorption length of the generation beam. In another example, a probe beam 152 formed by a HeNe laser is maintained at a power less than or equal to $\frac{1}{4}^{th}$ power of generation beam 151 formed by an Ar laser (having an absorption length 1.2 $\mu$m that is $\frac{1}{4}^{th}$ the 3.0 $\mu$m length of the HeNe laser beam). In the just-described implementation, the power of the reflected portion of probe beam 152 is maintained large enough (by having a sufficiently large power of probe beam 152) to be detected with sufficient accuracy (e.g. with error of 5% or less) required for reflectance measurements as described herein.

In one variant of this implementation, the difference between the generation rates of beams 151 and 152 is one order of magnitude only at surface 153 (FIG. 1C). In a second variant, the order of magnitude difference is maintained throughout junction depth "Zj" of doped region 130 in wafer 105/106, e.g. throughout depth of 0.3 microns. In a third variant, the order of magnitude difference is maintained throughout a predetermined fraction (e.g. ½) of the junction depth Zj.

In one embodiment, each measurement for a wafer 104/105/106 is compared (in act 260 in FIG. 2A) with a predetermined range, and if any measurement falls outside the range, the wafer is rejected. In one implementation, computer 103C displays on monitor 103M a message indicating that measurements identify a wafer 104/105/106 as unacceptable, while in another implementation computer 103C drives a signal to a robot (not shown) to move wafer 104/105/106 into a bin of rejected wafers (if rejected). The acceptable wafers are processed further in the normal manner (see act 262 in FIG. 2A).

In addition, act 240 is used in one implementation to screen out starting wafers formed of bare silicon. When defects in such bare silicon are identified at the beginning, the method results in correction of the wafer fabrication process to ensure a sufficiently low defect level and eliminate the cost and use of a starting wafer 106 formed of epitaxial material. Starting wafers formed of pure silicon (also called "prime wafers") are processed by profiler 103 in a manner identical to starting wafer 104 as described herein.

Two or more of the interference measurements made in act 243 (FIG. 2A) may be used (in an operation 250) to look up a material property of wafer 104/105/106. For example, in the front surface embodiment, profiler 103 performs acts 251–253 illustrated in FIG. 2C. Specifically, in act 251, profiler 103 transforms the interference measurement, e.g. by multiplying with a constant. Note that act 251 is an optional act, for example if the predetermined data is scaled.

Next, in act 252, profiler 103 performs look up of predetermined data by determining a location 2551 (FIG. 2D) of the measurement (either the raw measurement or the scaled measurement, depending on whether the predetermined data is scaled) on a line 255. In performing the lookup, the measured amplitude is used with a sign that is determined from the measured phase, e.g. if the phase measurement is less than 180 degrees, the measured amplitude is used as a positive value, and otherwise as a negative value. Note that a specific value of the phase measurement is not used in this embodiment (other than to determine the sign), although such a value is actually used in another embodiment (described below in reference to FIG. 6).

Profiler 103 uses a line (also called "curve") 255 that is a plot (along the y axis) of the measured signal (e.g. in microvolts) as a function of a material property (along the x axis), such as junction depth (for a selected concentration $n_e$ of excess carriers, as determined in this example, by generation beam power of 10 mW). Specifically, in act 253, profiler 103 reads off a value v1 (also called "first value") of the material property from the determined location. In the example illustrated in FIG. 2D, signal S1 (obtained by interference between the reflections by front surface and excess carriers) has a value of 10 $\mu$V, and profiler 103 finds a value v1=0.04 $\mu$m for the junction depth.

Figure 2E:
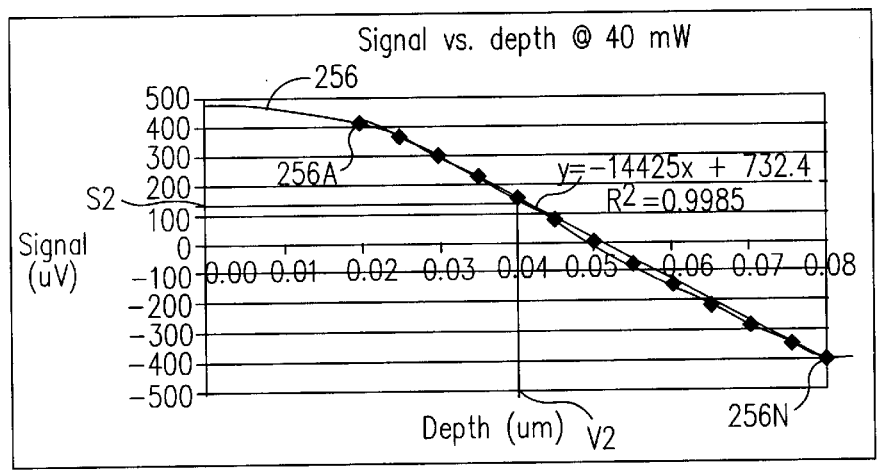
Figure 2F:
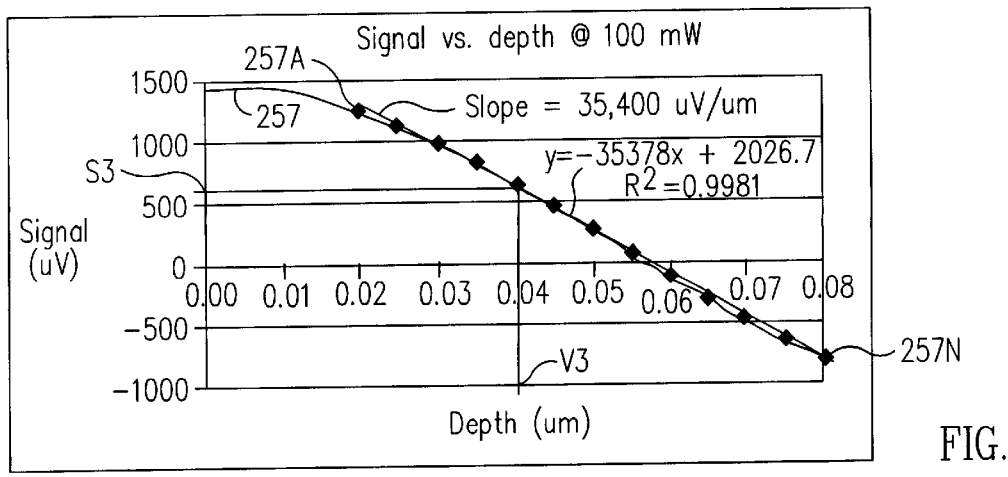

In the just-described example, programmed computer 103C can compare either S1 or v1 (in act 260 illustrated in FIG. 2A) with an appropriate one of ranges 40 to −20 and 0.03 to 0.05 $\mu$m to determine that the wafer is acceptable (in act 262). Profiler 103 (FIG. 1A) may perform act 241 (by increasing the generation beam power to 40 mW), and repeat acts 252 and 253, to find a second value v2 of the material property from another line 256 (FIG. 2E). In the example illustrated in FIG. 2E, profiler 103 uses an interference signal S2 of value 150 $\mu$V to again find a value v2=0.04 $\mu$m for the junction depth. Also, in the example in FIG. 2E, signal S2 is obtained by increasing the intensity of generation beam 151 to 40 mW (from the 10 mW used to obtain the interference signal of value S1).

Figure 3:
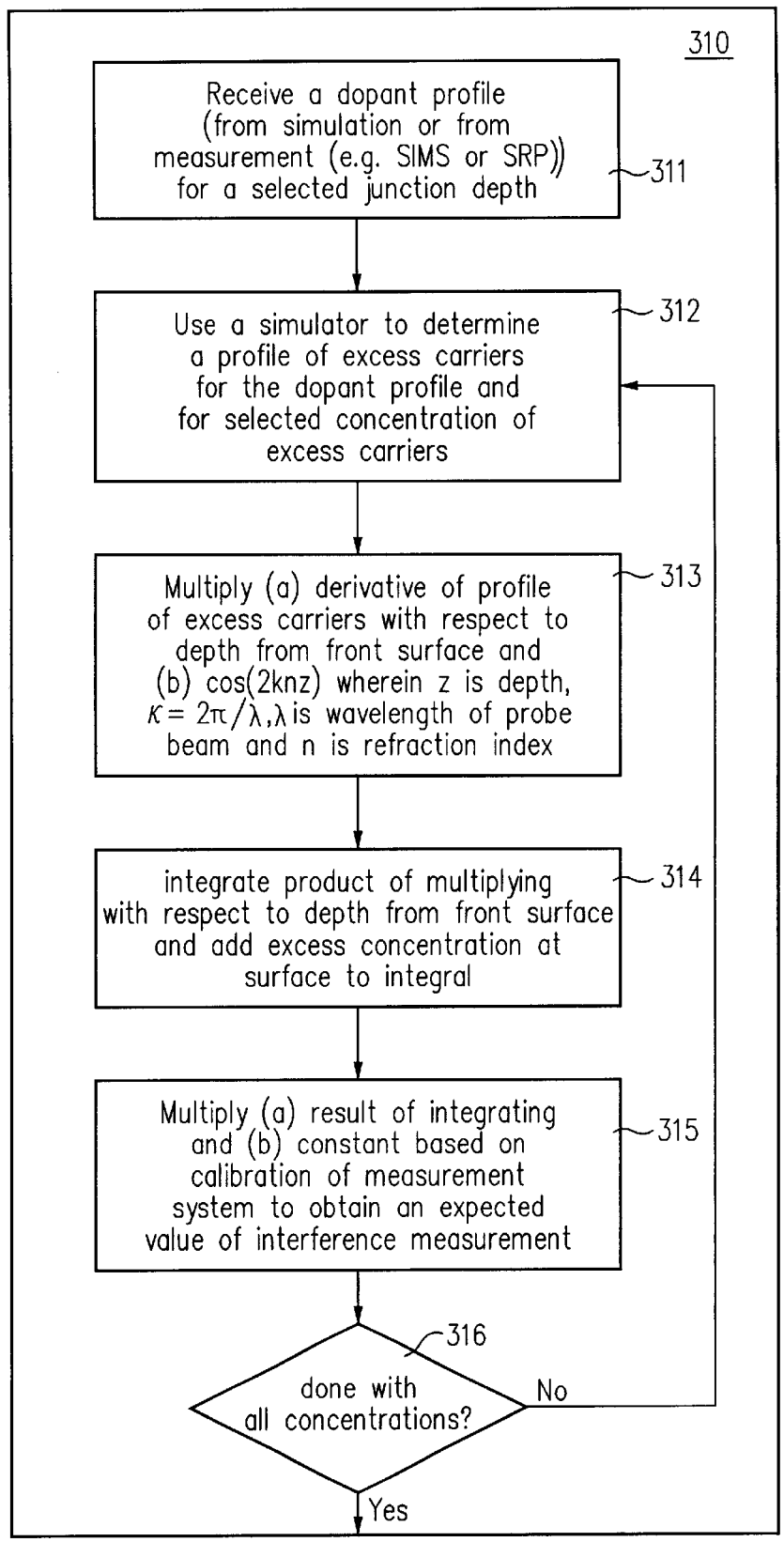
FIG. 3 illustrates, in a flowchart, generation of predetermined data in an optional act 210 (illustrated in FIG. 2A) performed by the profiler of FIG. 1A.

Graphs 2D–2F are computed using one or more methods of the type described below in reference to FIG. 3, wherein a doping profile is assumed. Simulated values for both amplitude and phase (e.g. phase of 0° and 180° results in positive and negative values respectively for the intensity) are then calculated (e.g. see act 315 described below) as a function of generation laser power and profile depth to obtain graphs 2D–2F. In practice, the real doping profile may deviate from the assumed profile. In this case, values v1, v2 and v3 may not be identical, and the three values may be averaged.

In one embodiment, the result is reported as the average va of the three values v1–v3, and the range vr (obtained as the difference between the maximum and the minimum among values v1–v3). In another embodiment, the result is reported as the average va of the three values v1–v3 and a standard deviation vsd from the average va. That is, vsd= square root $(((va-v1)^2+(va-v2)^2+(va-v3)^2)/9)$. The range or the standard deviation are also compared with acceptable values for range or standard deviation as may be provided in a manufacturing specification.

Measuring junction depths as described above provides an unexpected result, considering that at least one prior art reference, namely U.S. Pat. No. 4,854,710 granted to Opsal teaches that depth information cannot be obtained in the absence of a plasma wave (specifically, Opsal states in column 4, lines 33–35, "[h]owever, in applications where sample variations as a function of depth need to be studied, it is necessary to generate and study plasma waves").

Graphs (e.g. see lines 255–257 in FIGS. 2D–2F), that are used to determine a material property (or a process condition) can be generated in any way. In a first embodiment, a set of wafers (also called "reference wafers") is selected or prepared to have a range of material properties (by varying process conditions, such as implant energy, rose or anneal temperature), and thereafter profiler 103 is used to obtain interference measurements as described herein, and generate best-fit lines for each of the measurement conditions (e.g. for each generation beam power as described above). In a second embodiment, a number of wafers (also called "reference wafers") are subjected to intensity measurements in profiler 103 (as described above), followed by use of a conventional measurement technique, such as spreading resistance profiling (abbreviated as "SRP") to determine the actual doping profile therein.

In both embodiments, programmed computer 103C generates each of lines 255–257 (FIGS. 2D–2F) from intensity measurements under the same conditions (e.g. diffusive modulation) on the set of reference wafers having different material properties (e.g. junction depths in the range of 0.02 $\mu$m to 0.08 $\mu$m, at increments of 0.005 $\mu$m). The reference wafers may be prepared by ion implantation of species such as Boron, Arsenic, Phosphorous, or $BF_2$ at an energy range of 0.2 to 5 KeV and dosage of $1\times10^{15}/cm^2$, followed by annealing (e.g. for 10 seconds) at each of the temperatures in the range 900–1050° C., with 50° C. increments.

Thereafter, if the material properties are not known, SRPs are prepared by breaking the wafers to expose the ion-implanted layer followed by beveled lapping and probing to measure the profile of the concentration of active dopants as a function of depth. Therefore, at the end of the preparation of SRP, the graphs (e.g. FIG. 4A) provide a plot of the active dopant concentration (atoms/$cm^3$) along the y axis as a function of depth (in microns) along the x axis.

Therefore, profiler 103 obtains a number of measurements SA–SN (FIG. 2D) for each of points 255A–255N ($A \leq I \leq N$, N being the total number of measurements), with beams 151 and 152 coincident in the same region 120 (FIG. 1C) on each of the reference wafers. Thereafter, profiler 103 fits points 255A–255N to a curve 255 (e.g. represented by a linear approximation of the form y=−3.016x+130.88 in FIG. 2D). In a similar manner, profiler 103 generates points 256A–256N and 257A–257N for generation beam powers of 40 mW and 100 mW respectively, and thereafter generates the corresponding curves 256 and 257. Note that each of curves 255–257 is a sinusoidal curve that can be approximated by a straight line (as shown in the example in FIG. 2D) over a portion of the curve.

Alternatively, sinusoidal curves 255–257 that are obtained from curve fitting of points 255A–255N, 256A–256N and 257A–257N may be used directly, without a linear fit to determine a straight line. Use of sinusoidal curves 255–257 is more accurate than use of a linear approximation, although the linear approximation is simpler to implement. Also, instead of approximating a curve 255 with a straight line equation, a second or higher order differential equation can be fitted to the points, and the differential equation may be used to obtain the property measurement (in the manner described herein, as would be apparent to a person skilled in the art of computer programming). Moreover, instead of a reflectance measurement being used to measure a property of the semiconductor material, a change in the index of refraction can also be used in a similar manner.

After one or more of the above-described graphs (see FIGS. 2D–2F) are prepared, the material properties of a wafer under fabrication are determined by the above-described method 200 (FIG. 2A) without the need to break and lap the wafer, because profiler 103 simply uses the above-described graphs to generate measurements of material properties. Therefore, profiler 103 eliminates the cost associated with test wafers otherwise required by the prior art methods (for breaking and lapping).

Although in the above description, computer 103C has been described as performing various computations for the preparation of curves (e.g. curve 255 in FIG. 2D) used to measure material properties, such graphs can be prepared by another computer, or alternatively can be prepared by manually performing the above-described acts.

Moreover, although in one embodiment the above-described curves (e.g. FIGS. 2D–2F) are drawn, in another embodiment such graphs are not prepared and instead the reflectance measurements are simply used to perform the various acts of method 200, by use of equations related to such graphs. For example, instead of drawing a curve 255 (FIG. 2D), an equation for the curve is determined by fitting (as discussed above), and thereafter the equation is used to obtain the material property.

In one implementation, probe beam 152 (FIG. 1E) is a laser beam having a wavelength greater than 1.05 $\mu$m (the wavelength at which photons have approximately the same energy as the bandgap energy of silicon). Note that the wavelength of probe beam 152 depends on the bandgap energy and therefore on the specific material in wafer 105/106, and is different for germanium.

Figure 4B:
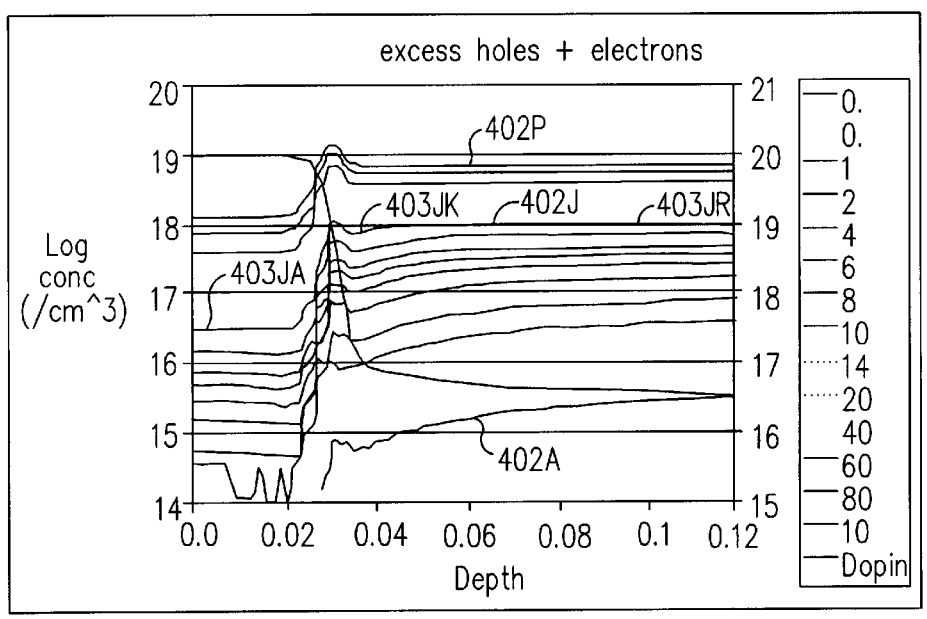
FIG. 4B illustrates, in a graph, a number of profiles of excess carriers (i.e. the concentration of excess carriers as a function of depth) for the dopant profile of FIG. 4A, obtained by performance of act 241 illustrated in FIG. 2A.

In one embodiment, the predetermined data for use in act 246 (described above) is prepared by performing method 310 (FIG. 3) that implements act 111. Specifically, in act 311, computer 103C (FIG. 1A) receives (see act 311 in FIG. 3) a dopant profile 401 (FIG. 4A) for a selected junction depth (e.g. a depth of 0.035 $\mu$m illustrated in FIG. 4A). Dopant profile 401 may be obtained by either simulation (e.g. by use of the simulators Atlas and Athena, both available from Silvaco International, Santa Clara, Calif.) or by a conventional method such as spreading resistance profile (SRP) or secondary ion mass spectrometry (SIMS). Next, computer 103C uses (see act 312 in FIG. 3) a simulator to determine a profile 402J (FIG. 4B) of excess carriers for a selected average concentration of excess carriers (e.g. as determined by a selected power of a generation beam), e.g. 10 mW.

Thereafter, for each of a number of points 403JA–403JR (wherein $A \leq K \leq R$, R being the total number of such points) computer 103C multiplies (as illustrated by act 313 in FIG. 3) the following two multiplicands to obtain a product: (1) derivative of profile 402J with respect to depth from front surface (i.e. dy/dz) and (2) cos (2 knz), wherein z is the depth, k=2$\pi$/$\lambda$, $\lambda$ is the wavelength of the probe beam, and n is the index of refraction of the substrate.

Figure 4C:
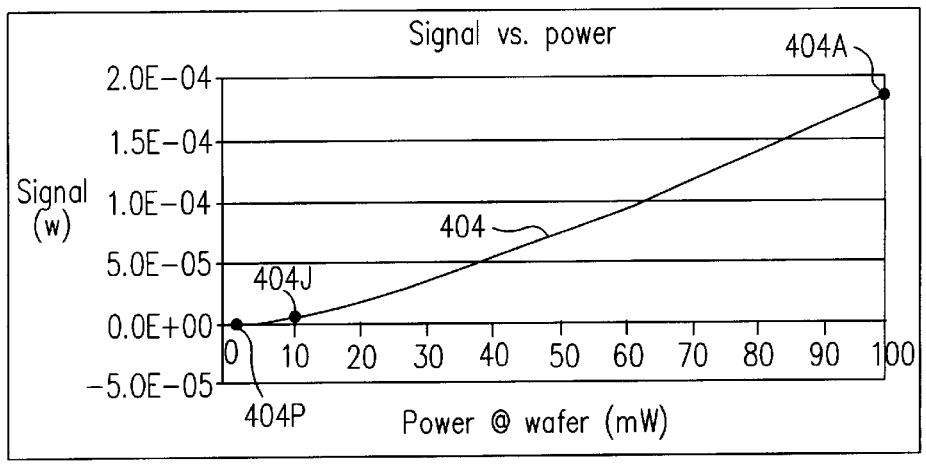
FIG. 4C illustrates, in a graph, a simulated value of an interference measurement as a function of the intensity (also called "power") of the generation beam, obtained by performance of acts 313–315 illustrated in FIG. 3.

Next, computer 103C integrates (see act 314 in FIG. 3) the products (at each of points 403JA–403JR) with respect to depth z, adds the value of the excess carrier concentration at the surface, and multiplies (see act 315 in FIG. 3) the result of integrating with a constant. The constant is based on calibration of profiler 103, and provides the simulated value of the signal obtained by interference between portions of probe beam 152 that are reflected by the excess carriers and by front surface 153. Computer 103C may (in an optional act not illustrated in FIG. 3) plot a point 404J (FIG. 4C) in a graph that shows the simulated value along the y axis as a function of generation beam power along the x axis.

Then, computer 103C checks (in act 316 in FIG. 3) if a number of selected powers of generation beam 151 (FIG. 1E) have been processed. as described above for profile 403J. If not, computer 103C returns to act 312 (and performs acts 313–315) for another profile (for another selected power of generation beam 151). In one example, computer 103C performs acts 312–315 for each power in the set of 0.1, 0.2, 1, 2, 4, 6, 8, 10, 14, 20, 40, 60, 80 and 100 mW (a range over which generation beam power is expected to be varied), thereby to obtain each of a corresponding number of points 404A–404P, wherein $A \leq J \leq P$, P being the total number of such profiles.

Figure 4D:
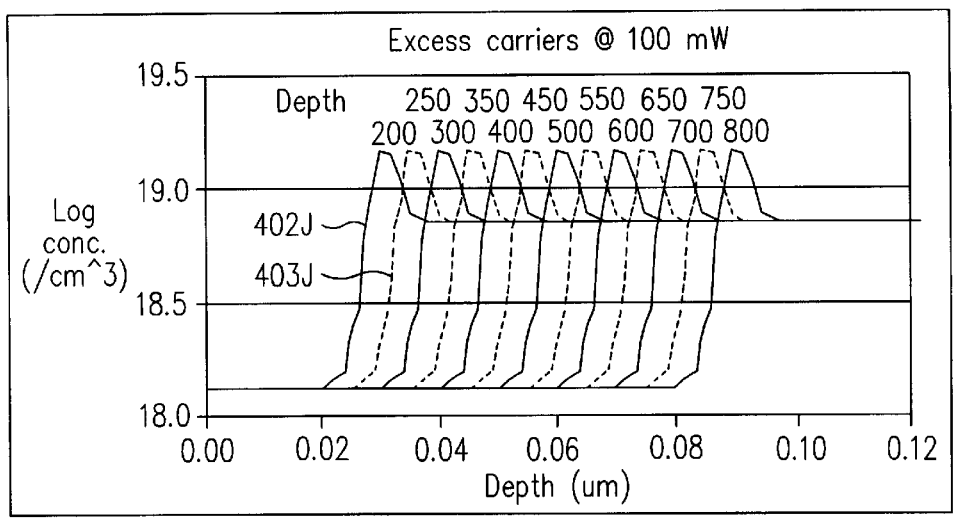
FIG. 4D illustrates, in a graph, a number of excess carrier profiles for the doping profile of FIG. 4A, as the doping profile (see FIG. 4A) is shifted progressively deeper into the semiconductor.
Figure 4E:
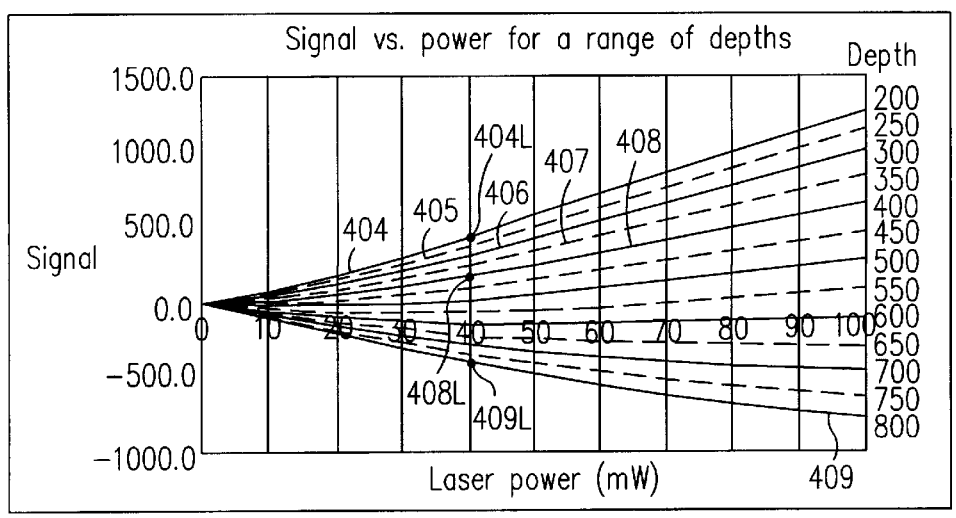
FIG. 4E illustrates, in a graph, a number of curves showing simulated value of interference measurements for different intensities of the generation beam, at different junction depths.

Thereafter, computer 103C draws a line 404 (FIG. 4C) that fits the points 404A–404P. Computer 103C repeats method 310 (i.e. acts 311–316 described above) for each of a number of different junction depths. Note that instead of generating depth profiles for each of the different junction depths by SRP or by simulation, the excess carrier profiles of act 312 can be generated by simply offsetting each of profiles 402A–402P (FIG. 4B) by the increment injunction depth (e.g. shifting each profile 402J to the right by a distance of 0.005 μm on the x axis, as illustrated by profile 403J in FIG. 4D). Thereafter, the shifted profiles are processed as described above in reference to acts 313–315 (FIG. 3) to obtain another line (e.g. line 405 illustrated in FIG. 4E) that relates the generation beam power to the simulated value of the interference signal. In this manner several lines 404–409 are obtained (see FIG. 4E).

Next, for a given power of generation beam 151 (e.g. power 90 mW), computer 103C reads off a number of points on lines 404–409 to determine the simulated value of the interference signal for each of a number of junction depths. For example, simulated values for points 404L–409L are read off for each of junction depths 0.020–0.080 μm at increments of 0.005 μm. Thereafter, computer 103C plots points 404L–409L on a graph of simulated value of the interference signal as a function of junction depth (e.g. see FIG. 2E, wherein points 256A–256N correspond to points 404L–409L), and draws a line (e.g. line 256) that best fits the points. Computer 103C prepares similar graphs for each concentration of the excess carriers (e.g. for each of a number of generation beam powers), and thereafter uses the graphs as described above in reference to act 246 (FIG. 2A).

Figure 4F:
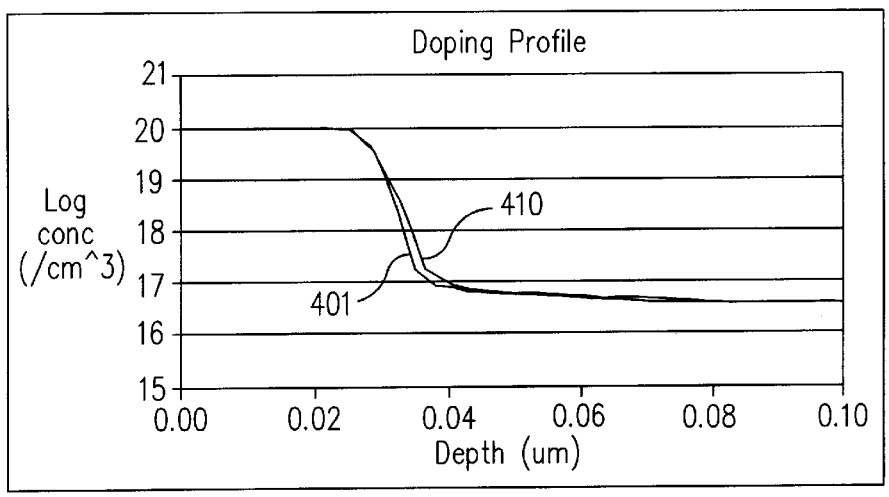
FIG. 4F illustrates, in a graph, two similar doping profiles, one identical to the profile shown in FIG. 4A and the other having a slightly shallower slope than the profile shown in FIG. 4A.

Computer 103C also prepares similar graphs for doping profiles that are similar to original profile 401 (FIG. 4A), but are modified by making the original profile deeper (e.g. see profile 410 in FIG. 4F) or shallower. In one example, an original profile 401 (FIG. 4A) is again used to prepare the similar profiles that are deeper or shallower, in accordance with the following procedure. The depth values were multiplied by a constant to expand the depth along x axis (in the example, the constant was 1.25). This makes the scaled profile (not shown) deeper, since each doping point is 1.25 times deeper than it was in the original profile 401. The depth values are then shifted by a constant (e.g. in this case 70 angstroms) so that the modified profile 410 (FIG. 4F) begins at the same point as original profile 401.

In one embodiment, a line 255 (FIG. 2D) showing interference signal vs. generation beam power is obtained, e.g. by measurements at the center of a 200 mm diameter wafer. The interference signal is then measured at a number of points, e.g. at points that are spaced 1 mm apart, at each of three generation beam powers of 10, 40 and 100 mW, along a diameter scan of the wafer. Lines 255–257 (FIGS. 2D–2F) are thereafter used to determine the doping profile within the wafer at each point within the scan. In this manner, the profile across the wafer may be determined to be uniform (e.g. falls within certain preset limits, such as 10% variation in the depth at which a concentration of $10^{18}$ dopant atoms per cubic centimeter is present).

Moreover, shifts in peak doping level are equivalent to a change in the slope of the profile 401 (FIG. 4A) of active dopants. For example, a 10% increase in peak doping is equivalent to a 10% increase in the slope of profile 401 (FIG. 4A). Hence, the peak doping sensitivity of the interference signal can be characterized, and used to measure the peak doping in a manner equivalent to that described above in reference to FIG. 3 for measuring a change in the junction depth.

In the first embodiment wherein a portion of probe beam 152 reflected by front surface 153 (FIG. 1E) interferes with another portion reflected by excess carriers. probe beam 152 is generated by a laser 501 (FIG. 5), that can be a conventional laser diode, such as a 1.48 mm wavelength InGaAs diode with a maximum power of 70 mW made by Hewlett-Packard of Palo Alto, Calif. In a second embodiment wherein probe beam 152 is interfered with a phase variable beam, laser 501 is a distributed Bragg reflector (DBR) AlGaAs laser with a wavelength of 1083 nm and a power of 50 mW (Spectra Diode Labs, San Jose, Calif).

A DBR laser is used in the second embodiment because it has a coherence length in excess of a meter. This simplifies interferometer design, since the reference beam length is not critical as long as the difference in path length between the reference beam path and the probe beam path is shorter than the coherence length (the probe beam path length is twice the distance from beam splitter 512 to the wafer 516; the reference beam path length is twice the distance from beam splitter 512 to mirror 513).

The output of laser 501 is collimated using lens 502 to provide a collimated beam 503 with a diameter of 3 mm. Lens 502 can be, for example, part number WT-CY3-163-10B-0.5 available from Wave Optics, Mountain View, Calif. In one embodiment, a generation beam 151 is created by an above bandgap laser 505, such as an AlGaAs diode laser with a wavelength of 830 nm and power of 200 mW, available from Spectra Diode Labs, San Jose, Calif. Profiler 103 includes a lens 507, which is part number 06GLC002/810 available from Milles Griot Corporation, Irvine, Calif. Lens 507 collimates the beam from laser 505 to generate a collimated beam 151 with a diameter of 3 mm. Lens 507 is mounted on a positioner (not shown) for providing motion to beam 151 with respect to beam 152.

The relation between wavelengths of beams 151 and 152 produced by lasers 501 and 505 is a critical aspect in one embodiment and leads to unexpected results, for example when beam 151 contains photons having energy above silicon's bandgap energy and beam 152 contains photons having energy approximately the same as or less than the bandgap energy. In this example, for a silicon wafer the 830 nm and 1083 nm wavelength beams provide one or more benefits described herein.

Wavelength 830 nm is considered particularly suitable for generation beam 151 because the absorption length in silicon is about 15 microns. Thus, the absorption length is much greater than the junction depth, and creation of excess charge carriers is nearly uniform over the depth of concern in the measurement. Because the photon energy is close to the bandgap energy, photon generation is more efficient, with less energy going directly into heating the semiconductor.

Also, the absorption length at wavelength 1083 nm is about 300 microns, and therefore the number of excess carriers being created by such a probe beam is sufficiently low to ensure minimum perturbation to the excess carrier distribution. Moreover, the absorption length at wavelength 1083 is short enough that very little reflection from a back surface of the wafer is seen (wafers are typically 600–800 microns thick), since the back surface reflection can potentially cause spurious signals.

Beams 151 and 152 are combined using dichroic splitter 510 (such as a partially transmissive mirror (e.g. part number 1918-b available from Dominar of Santa Clara, Calif.), forming a superposed beam 511. Beam 511 passes through a 50:50 beam splitter 512 (e.g. part number 2005 from Dominar ) that directs a portion of beam 511 to detectors 522a and 522b (via filter 520 and polarizing beam splitter 521), for use in measurement of an interference signal. The remainder of beam 511 passes through a 90:10 beam splitter 514 (available from Precision Applied Products of Fullerton, Calif., by specifying 93.3% transmission at 0.83 microns wavelength and 90% transmission at 1.48 microns wavelength), and an objective lens 515 (such as a 100×, 0.8 NA lens made by Olympus of Tokyo Japan). Objective lens 515 focuses the combined beam 511 onto wafer 516.

Note that the specifications for beam splitter 514 are selected based on the wavelengths of the generation and probe beams to ensure that a majority of the power is transmitted and a smaller amount (e.g. 10%) of the power is reflected. Note also that probe beam 152 is focused only in a carrier creation region 120 (FIG. 1E) that is formed by focusing generation beam 151 (FIG. 5). Specifically, because of chromatic aberration, the focal planes of beams 151 and 152 differ slightly. The size of the focal spot for beam 152 is smaller than the size of the focal spot for beam 151 by virtue of the shorter wavelength of beam 151. If wafer 516 is placed in the focal plane of beam 152, beam 151 will be slightly out of focus and its spot on front surface 153 (FIG. 1E) of wafer 516 (FIG. 5) will be larger in diameter and fully overlay the focal spot of beam 152.

Light reflected from wafer 516 passes back through objective lens 515, 90:10 beam splitter 514, and into 50:50 beam splitter 512. Half of the light reaching beam splitter 512 is directed back through filter 520 (which is a bandpass filter that blocks the light from beam 151 but passes the light from beam 152). Filter 520 can be, for example, Schott glass RG830, available from Spindler & Hoyer Corporation of Goettingen, Germany. Alternately, filter 520 can be a narrow-band pass filter with a center wavelength of 1080 nm, available from Melles Griot of Irvine, Calif.

Filter 520 removes photons of generation beam 151 from the reflected beam, thereby allowing detector 522a to see only the photons of probe beam 152. Filter 520 is a critical component in one embodiment and provides the unexpected result of eliminating feed-through of the modulated signal (generated by beam 151) to detector 522a that would otherwise be present when using a prior art system. In this particular implementation, germanium is used in photo detector 522a to provide sensitivity to photons of wavelength 1083 nanometers that are generated by laser 501.

In the first embodiment, a reference beam is formed by a portion of probe beam 152 that reflects from front surface 153 (FIG. 1E), and 50:50 beam splitter 512 diverts 50% of the reflected beam from front surface 153 toward detector 522a. Note that in the First embodiment, beam splitter 521, detector 522b, and amplifier 523b are not used (i.e. are not present).

Detector 522a is a photocell (such as a photodiode or a phototransistor, e.g. J16-8SP-RO5M-HS from EG&G Judson of Montgomeryville, Pa., USA) that converts the incident interference signal into a current. Amplifier 523a converts the current to an amplified current which is then sent to an amplifier 524 that in turn is coupled to a lock-in amplifier 525 (such as model 830 available from Stanford Research Systems, Sunnyvale, Calif.).

Lock-in amplifier 525 includes a reference oscillator at the lock-in detection frequency. This oscillator is coupled to a laser driver 526 to provide a signal to laser 515 that is modulated at the same frequency as the signal provided by lock-in amplifier 525. Lock-in amplifier 525 provides a signal indicating the amplitude as well as phase of reflected beam with respect to modulation by laser driver 526 to a processor 527, such as a personal computer running software to capture and display the signal in an appropriate manner (e.g. in a graph). The signal may also be stored in the personal computer (e.g. in a database on the hard disk) for later processing.

In one implementation, personal computer 527 has a line 528 that is coupled to lines 107 and 108 (described above in reference to FIG 1A) thereby to control the acts performed by ion implanter 101 and rapid thermal annealer 102 based on measurement of one or more material properties as described herein.

Beam splitter 514 diverts 10% of the return beam from wafer 516 via a lens 517 (such as tube lens 81845 available from—Nikon of Tokyo, Japan) to a camera 518 (such as a CCD camera, e.g. model 85400 available from FJW Industries of Palatine, Ill.). The signal provided by camera 518 is fed into a vision system (not shown in FIG. 5), such as model ASP-60CR-11-S available from Cognex Corporation, Boston, Mass.

Positioning of wafer 516 with respect to the combined beam 511 is accomplished using a microscope that includes stage 529, objective lens 515, beam splitter 514, lens 517 and camera 518. Stage 529 can be used is used to move wafer 106 relative to beam 511 in the X, Y and Z directions. Specifically, stage 529 can be used to move wafer 516 in the vertical direction along the Z axis to adjust focus, and in a horizontal plane to adjust the position of region 120 of FIG. 1E relative to beam 511.

In a second embodiment, an independent beam 531 having a variable phase is used as a reference beam (instead of using just portion 162 that is reflected by front surface 153). Specifically, reference beam 531 is a portion of probe beam 152, and compensator 506 rotates the polarization 90°, so that the polarization of reference beam 531 is orthogonal to the polarization of portion 162 reflected from wafer surface 153. In one implementation, compensator 506 is model 5540, available from New Focus Inc., Santa Clara, Calif. The phase of reference beam 531 is varied by adjusting the path length using piezoelectric positioner 504 that is located behind mirror 513. The phase and polarization of beam 531 can be. changed independent of probe beam portion 162.

A measurement (also called "front surface reference") of interference between the reference beam and reflection from the front surface is a non-wave signal (also referred to as a "dc" signal) that varies at the same rate as variation of the length of the path of the reference beam (also called "reference arm length"), e.g. by a piezoelectric device 504 that moves mirror 513. In the embodiment illustrated in FIG. 5, the front surface reference measurement is provided by sum detector 522a.

Another measurement (also called "excess carrier reference measurement") of interference between the reference beam and reflection by the excess carriers is signal that is modulated at the same frequency as generation beam 151 and that is delayed in phase as compared to the front surface reference. The difference between the two measurements provides the phase difference that indicates the absolute junction depth as described below. In the embodiment illustrated in FIG. 5, the excess carrier reference measurement is provided by lock-in amplifier 525.

Specifically, in the second embodiment, the path length (also called "reference arm length") of reference beam 531 (to and from front surface 153) is set to be an integral multiple of the probe beam wavelength. This is done by adjusting the position of mirror 513 by applying a voltage to piezoelectric element 504 so that the signal in sum detector 522a is at maximum. The maximum occurs when there is constructive interference between beam 531 and reflection 162 of probe beam 152 from front surface 153.

Next, measurements at sum detector 522*a* and at lock-in amplifier 525 are recorded (note that the lock-in amplifier signal corresponds to the difference between the outputs of detectors 522*a* and 522*b*). Thereafter, the reference arm length is incremented a small fraction of a wavelength, and these two measurements are again recorded. The reference arm length is changed by changing the voltage applied to piezoelectric element 504 that controls the location of mirror 513.

Figure 7A:
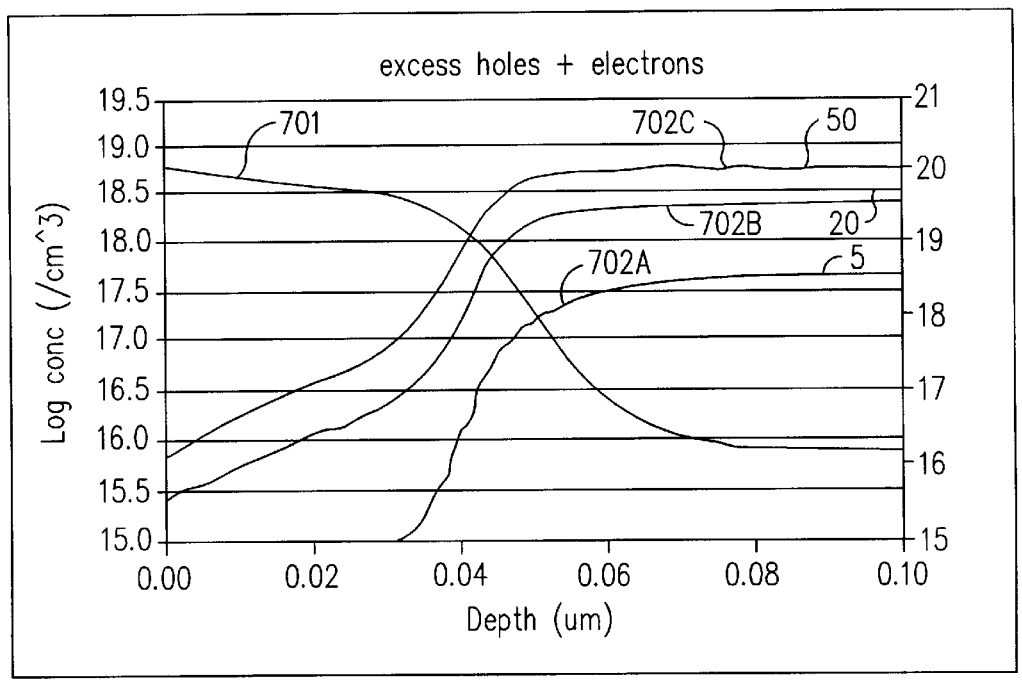
FIG 7A illustrates, in a graph, the active doping profile and excess carrier concentration as function of depth at various generation laser powers for a typical ion implant (boron, 500 eV, $1 \times 10^{15}$ ions/cm$^2$, annealed 10 seconds at 1000° C.).
Figure 7B:
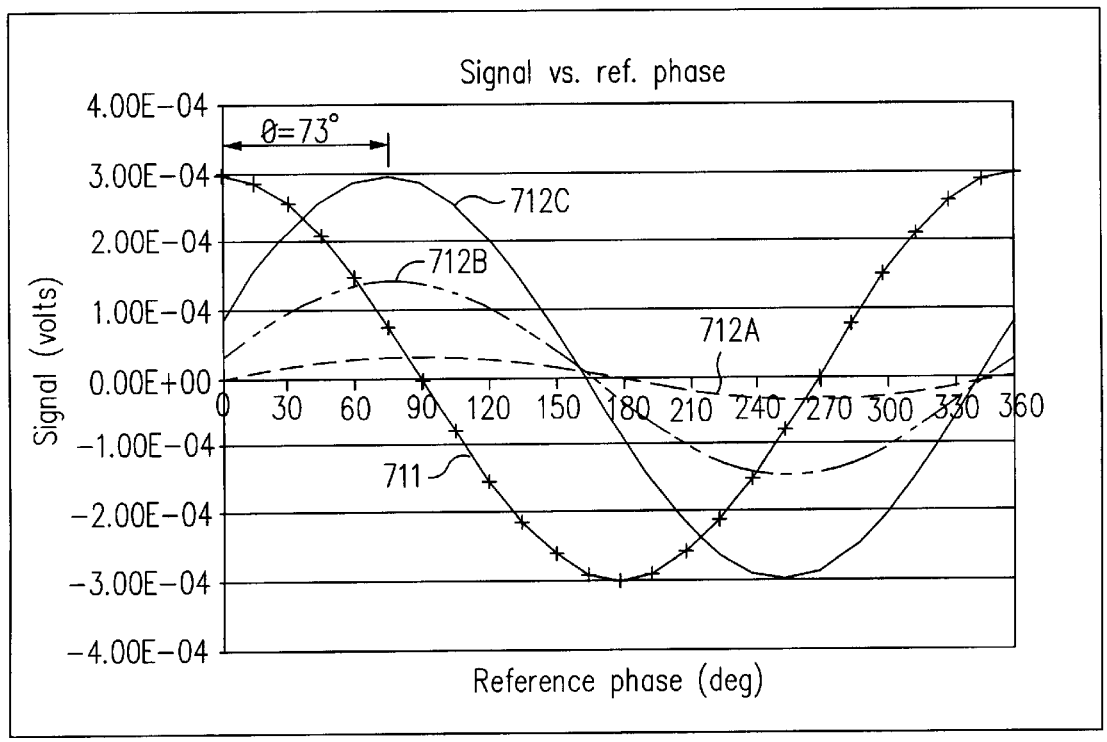
FIG. 7B illustrates, in a graph, the intensity measurement of the excess carrier reflection as a function of reference arm phase for the 5, 20 and 50 mW power levels shown in FIG. 7A, and also the intensity measurement of the front surface reflection.

Such measurements may be repeated over several intervals of wavelength of probe beam 152, so that a smooth curve is obtained (over a half-wavelength interval; a curve having greater than 10:1 signal-to-noise ratio is considered smooth in one embodiment). The measurements by each of lock-in amplifier 525 and detector 522*a* are plotted to obtain two curves, one for each of the front surface reference measurement and the excess carrier reference measurement that are plotted against normalized reference arm length (obtained by dividing the reference arm length by the wavelength of probe beam and multiplying by the refractive index of the semiconductor material) as illustrated in FIG. 7B.

Thereafter, the phase difference θ is measured, e.g. to be 73 degrees, and the phase difference when divided by 360 degrees and multiplied by a constant (probe beam wavelength divided by index of refraction in the semiconductor) yields the absolute value of the junction depth (the depth at which the concentration of dopants is equal to a predetermined concentration, e.g. $10^{18}/cm^3$). The phase shift of 73° corresponds to a junction depth of 0.044 μm, matching well with profile 701 (discussed above).

The laser power may then be changed, and the measurements above repeated to measure a junction depth at a different active doping concentration. In this manner, the doping profile is determined as a plot of the results of the measurements at different laser powers.

Figure 6:
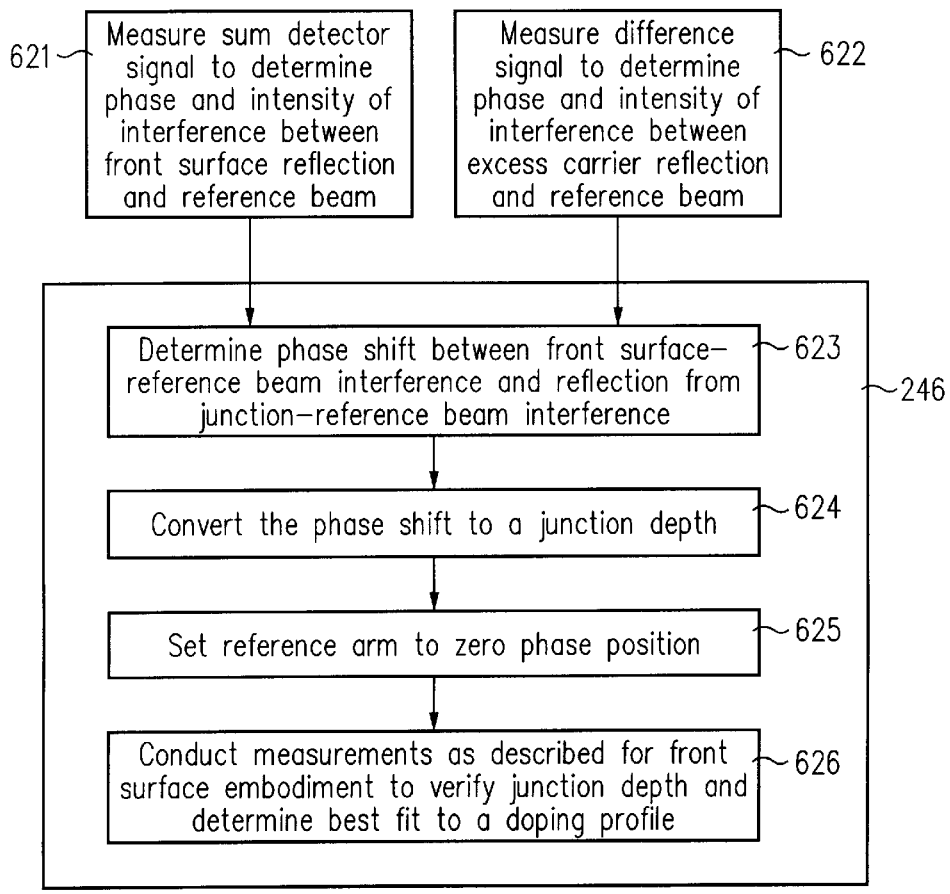
FIG. 6 illustrates, in a flow chart, another use of the measurements in optional act 250 (illustrated in FIG. 2A) performed by the profiler of FIG. 1A.

In the second embodiment, operation 246 is performed by the acts illustrated in FIG. 6. Specifically, two interference signals are simultaneously measured. In act 621 the output of sum detector 522*a* (see FIG. 5) provides a measure of the reference beam phase with respect to front surface 153 of the wafer (see FIG. 1E). Moreover, in act 622 the output of the lock-in amplifier 525 (see FIG. 5) gives the difference signal based on the interference between the reflection 163 by excess carriers at the junction and the reference beam 531.

In act 623, both outputs are plotted on the same graph (e.g. FIG. 7B), and the phase shift between the two outputs is measured. In act 624, the phase shift is converted to a junction depth based on knowledge of the laser wavelength and the semiconductor index of refraction according to the formula $$z_j = \frac{(\text{phase\_shift})}{2kn}$$

where n is the index of refraction of the semiconductor and $k=(2\pi)/\lambda$, where $\lambda$ is the wavelength of probe beam 152.

In act 625, reference arm phase is then set to the position of maximum signal in detector 522*a*, corresponding to the reference beam path length being equal to the surface reflection path length. This makes the measurement output equivalent to that obtained using the front surface reflection method (first embodiment). In operation 626, one or more acts (described above in reference to the first embodiment) are used to verify the junction depth, and to determine the best fit to a doping profile.

Line 701 (FIG. 7A) illustrates a typical doping profile, measured using SRP from an ion implant under the conditions of 500 eV Boron ions at a dose of $1\times10^{15}$ ions/$cm^2$, annealed 10 seconds at 1000° C. Curves 702A–702C show the simulated excess carrier concentration /$cm^3$ for profile 701, with respective laser powers of 5 mW (for curve 702A), 20 mW (for curve 702B) and 50 mW (for curve 702C), with a spot diameter of 2 μm. Applying eqn. (16) to the profiles for the excess carrier distributions at 5, 20 and 50 mW provides expected signals as a function of reference arm phase of curves 712A, 712B, and 712C respectively.

Also shown is curve 711, the cosine of the reference arm phase, corresponding to equation (19), with the zero point defined as $z_{ref}=z_s$.

A phase shift of θ=73° is observed in FIG. 7B. Solving using the above defined procedure, $$z_j = \frac{(\text{phase\_shift})}{2kn},$$

where n=3.42 is the index of refraction of silicon and $k=(2\pi)/\lambda$, where the probe beam wavelength λ=1.48 μm, providing the above-mentioned value of 440 angstroms.

The advantage of the second embodiment over the front-reflection method (first embodiment) is that it provides an absolute measure of the active carrier concentration depth corresponding to a set generation laser power level in terms of the phase shift of the cosine-shaped signal in the plot of signal versus reference arm length. Its disadvantages are the added complexity of the reference arm and the necessity of using a laser with a coherence length longer than the difference in physical length between the two arms of the interferometer, those being the reference arm and the measurement arm.

Note that although in one specific embodiment, a reference beam having a variable phase has been described as being generated by an interferometer having two arms, any other device that can generate a variable phase reference beam can be used in accordance with the principles described herein.

As noted above, in the second embodiment, interference with a reference beam 531 having a variable phase is used, and 50% of the light in probe beam 152 is redirected towards compensator 506 and mirror 513 thereby to form the reference beam arm of the interferometer. Compensator 506 is used to set the polarization of reference beam 531 with respect to the remaining portion of probe beam 152 that is redirected toward objective lens 515 and wafer 516. Mirror 513 is mounted on a piezoelectric element 504, thereby to allow the length of the reference beam path to be adjusted electronically over the range of at least a wavelength (or several wavelengths if the signal is to be averaged over several cycles).

The polarization of reference beam 531 is set orthogonal to probe beam 152 (by compensator 506). Probe beam 152 and reference beam 531 interfere in polarizing beam splitter 521, which is oriented at 45° with respect to the polarization of the two beams 532 and 531 (wherein beam 532 represents the arm of the interferometer including the path to wafer front surface 153). This provides sum and difference beams at detectors 523*a* and 523*b*. The detector currents, which are proportional to the powers at the detectors, are converted to voltages in transimpedance amplifiers 523*a* and 523*b*. Amplifier 524 takes the difference in the voltages from amplifiers 523*a* and 523*b*. The difference signal is fed to lock-in amplifier 525 thereby to generate the interference signal being supplied to processor 527.

The physical principles that relate to the methods described above are as follows. The electric field at each of detectors 522a and 522b is $$E = E_s + E_j \pm E_{ref} \quad (1)$$

where $E_s$ is the portion 162 of probe beam 152 reflected from front surface 153 (not including the excess carrier concentration at the surface), and $E_j$ is the portion 163 of probe beam 152 reflected by excess carriers in the junction (including the excess carriers near the surface), and $E_{ref}$ is the component from the variable phase reference beam which is zero if there is no variable phase reference beam.

The ± in equation 1 comes from the polarizing beam splitter 521 (FIG. 5) that provides sum and difference components to the two detectors 522a and 522b. The power in these detectors is $$P^\pm = (E_s + E_j \pm E_{ref})(E_s^* + E_j^* \pm E_{ref}^*) \quad (2)$$

Multiplying out equation 2, the signals in the sum and difference detectors 522a and 522b are $$P^\pm = |E_s|^2 + |E_j|^2 + |E_{ref}|^2 + (E_s E_j^* + E_s^* E_j) \pm (E_s E_{ref}^* + E_s^* E_{ref}) \pm (E_j E_{ref}^* + E_j^* E_{ref}) \quad (3)$$

In the first embodiment, the surface reflection 162 is interfered with the reflection 163 by the excess carriers, and hence the reference field is $E_{ref}$ is zero. Therefore, the squared amplitude of the reflection 163 from the junction is negligible, and the squared amplitude of the reflection 162 from front surface 153 does not appear at the modulation frequency. Thus, the only component seen in lock-in amplifier 525 (FIG. 5) is $$P_{s-j} = (E_s E_j^* + E_s^* E_j) \quad (4a)$$

In the second embodiment, a reflection of the reference beam 531 by mirror 513 is interfered with the reflection 163 from the junction, the signal at the lock-in amplifier 525 is the difference between the signals from the plus and minus detector (e.g. from detectors 522a and 522b). Taking the difference, and recognizing that the $(E_s E_{ref}^* + E_s^* E_{ref})$ term does not appear at the modulation frequency the resulting signal is $$P_{ref-j} = P^+ - P^- = 2(E_j E_{ref}^* + E_j^* E_{ref}) \quad (5a)$$

Finally, the junction term may be considered as a continuous distribution. Alternately, it may be considered to be composed of a surface and profile term, yielding $$P_{s-j} = [(E_{js} + E_{jp})E_s^* + (E_{js}^* + E_{jp}^*)E_s] \quad (4b)$$

$$P_{ref-j} = 2[(E_{js} + E_{jp})E_{ref}^* + (E_{js}^* + E_{jp}^*)E_{ref}] \quad (5b)$$

Ignoring the time dependent part of propagation, the incident light from probe beam 152 has a phase at the surface of $$E_{in} = E_0 e^{jkz_s} \quad (6)$$

where the amplitude is $E_0 = \sqrt{P}$, with P the power of probe beam 152 at the wafer surface, and the wave number is $k = 2\pi/\lambda$, with $\lambda$ the wavelength of probe beam 152. The reflected electric field from the boundary between air and the silicon surface 153 (FIG. 1E) is $$E_S = \frac{1 - n_{s0}}{1 + n_{s0}} E_0 e^{2jkz_s} \quad (7)$$

where the amplitude is $E_0 = \sqrt{P}$, with P the power of probe beam 152 at wafer surface 153, $n_{s0}$ is the index of refraction of silicon, $z_s$ is the path length to the silicon surface, and the wave number is $k = 2\pi/\lambda$, with $\lambda$ the wavelength of the probe beam 1521

As noted above, excess carrier profile 164 (FIG. 1D) may be modeled as a set of thin layers of excess carriers, such as layers 164A–164T (FIG. 1E). The reflection from interface 165J between the $j^{th}$ layer 164J and $(j+1)^{th}$ layer 164J+1 is $$r_j = \frac{n_j - n_{j+1}}{n_j + n_{j+1}} \approx \frac{\beta}{2n_{s0}}(N_j - N_{j+1}) = -\frac{\beta}{2n_{s0}}\frac{\Delta N}{\Delta z}\Delta z \approx -\frac{\beta}{2n_{s0}}\frac{dN}{dz}dz \quad (8)$$

where the index of refraction of a layer is $n_j = n_{s0} + \Delta n_j$, where the change in index due to the excess carrier concentration is $\Delta n_j = \beta N_j$, where $N_j$ is the excess carrier concentration in layer 164J and the factor $\beta$ is given by $$\beta = \frac{q^2 10^6}{2\varepsilon_s \varepsilon_0 m^* \omega^2} \quad (9)$$

where $q = 1.602 \times 10^{-19}$ is the electron charge, N is the carrier concentration per $cm^3$ (the factor of $10^6$ converts to per $m^3$ to allow use of MKS units), $\varepsilon_0 = 8.86 \times 10^{-12}$ Farads/meter is the dielectric constant of free space, $\varepsilon_s = 11.7$ is the relative dielectric constant of silicon, $m^* = 5 \times 10^{-31}$ kg is the effective carrier mass, and $\omega = 2\pi c/\lambda$ is the radial frequency, with $c = 3 \times 10^{10}$ cm/sec the speed of light. Note that concentration N is same as concentration $n_e$ that has been described above. The reflected electric field is the sum from all layers 164A–164T, $$E_j = t_s^2 \sum_i r_j E_0 e^{jk(2z_s + 2nz_f)} \quad (10)$$

where $z_s$ is the distance to the surface and $$t_s = 2\frac{\sqrt{n_{s0}}}{(1 + n_{s0})}$$

is the surface transmission. In the limit as the thickness of layer 164J approaches zero, applying 8 into 10, $$E_j = -(E_0 e^{j2kz_s})\frac{\beta}{2n_{s0}} t_s^2 \int_0^\infty e^{j2knz}\frac{dN}{dz}dz \quad (11)$$

If the surface excess carrier concentration rises from zero to the $N_s$ over a distance $z_f$ that is short compared to the wavelength, the integral in equation 11 can be broken into two parts, $$E_j = -(E_0 e^{j2kz_s})\frac{\beta}{2n_{s0}} t_s^2 \left[\int_0^{z_f} e^{j2knz}\left(\frac{N_s}{z_f}\right)dz + \int_{z_f}^\infty e^{j2knz}\frac{dN}{dz}dz\right] \quad (12)$$

which reduces to $$E_j = -(E_0 e^{j2kz_s})\frac{\beta}{2n_{s0}}t_s^2\left[N_s + \int_0^\infty e^{j2knz}\frac{dN}{dz}dz\right] \quad (13)$$

There are two terms in the above equation 13. One is from the near-surface, and depends only on the excess carrier concentration at the surface $N_s$. The second is the Fourier transform of the derivative of the excess carrier profile N. The electric field amplitude of the reference beam 531 is $$E_{ref}=E_0 e^{j2kz_{ref}} \quad (14)$$

where $z_{ref}$ is the length of the reference arm. Substitution into the above equations gives the signal power for interference between the surface and the excess carrier profile as $$P_{s-j} = \frac{(n_{s0}-1)\beta}{(n_{s0}+1)n_{s0}}t_s^2 E_0^2\left[N_s + \int_0^\infty \cos(2knz)\frac{dN}{dz}dz\right] \quad (15)$$

and for interference between the reference arm and the excess carrier profile, $$P_{ref-j} = -\frac{\beta}{n_{s0}}t_s^2 E_0^2\left[N_s\cos(2kz_{ref}) + \int_0^\infty \cos[2k(nz-z_{ref})]\frac{dN}{dz}dz\right] \quad (16)$$

Comparing equations (15) and (16), it is seen that when $z_{ref}=0$, the two equations are identical. This condition is met when the path length for the reference beam is equal to the path length to the front surface 153 (see FIG. 1E). This may be measured by simultaneously monitoring the output of either detector, 523a or 523b. This output gives a signal that is the interference between the reference beam and the surface reflection. This term is the second term from the right in equation (3), and takes the form $$(E_s E_{ref}^* + E_s^* E_{ref}) = 2P\cos[2k(Z_s - Z_{ref})] \quad (17)$$

When the reference and surface reflection paths are equal, the analysis to determine the semiconductor properties is identical for both embodiments.

The above-described methods can be used for measuring non-dopant amorphizing implants (defined to be implants of ions that cause damage but do not dope silicon). Examples of non-dopant amorphizing implants are implants that cause damage ,hen the high energy ions hit the crystal and stop. The ions have energies of several thousand eV, and the chemical bonds in the crystal are a few eV. Hence, the high energy ions are able to break the crystal lattice bonds, causing damage of silicon or germanium.

The purpose of these implants is as follows. To form a shallow ion implanted layer with a dopant atom such as boron, it is essential to confine the boron ion implant to a very shallow surface layer (e.g. only a few angstroms thick). Typically, boron atoms are accelerated to a very low potential (e.g. a few hundred eV) so that they stop within a few angstroms of the surface. However, because silicon has a crystal structure, certain directions present "channels"— long open paths through the crystal (typically the length of the crystal structure since channels are an inherent property of the crystal) in the space between the ordered silicon atoms. Some boron atoms will scatter off silicon atoms as they penetrate the silicon surface and follow the channels to considerably greater depths than desired.

To prevent channeling, a non-dopant implant—often precedes the boron implant. The non-dopant implant creates enough damage to destroy the crystal structure, forming an amorphous layer that is characterized by the amorphization depth (a depth to which the crystal structure has been destroyed by ion implant damage and replaced by the amorphous layer). Amorphization depth is difficult to measure by existing means. The typical method for measuring amorphization depth is to create a very thin cross-sectional slice and look at it with transmission electron microscopy. This is a slow, tedious and destructive procedure.

Figure 8A:
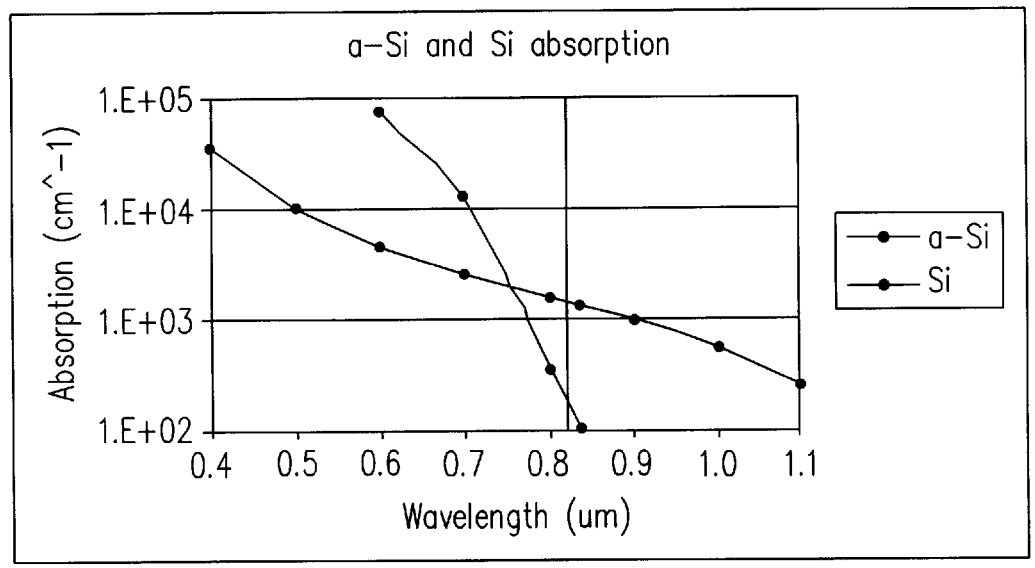
FIG. 8A illustrates, in a prior art graph, the absorption coefficient (inverse of the absorption length) for silicon and amorphous silicon (a-Si) as a function of wavelength in microns.

The amorphous layer may be modeled as a high bandgap layer. As stated by Sze, "Physics of Semiconductor Devices," page 827, "The difference between crystalline and amorphous Si is dramatic; the former has an indirect bandgap of 1.1 eV, whereas hydrogenated a-Si has an optical absorption characteristic that resembles the characteristic expected for a crystal with a direct bandgap of 1.6 eV." Prior art FIG. 8A (see FIG. 34 on page 828 of Sze), shows that at the preferred generation laser wavelength, 830 nm, the absorption in the amorphous silicon (line 801) is only about 10% of that in the silicon (line 802). Thus, the amorphous silicon may be modeled as a transparent layer in one embodiment.

Substituting into equation 15 for the signal in the case of interference with the surface (first embodiment), $$P_{s-j} = \frac{(n_{s0}-1)\beta}{(n_{s0}+1)n_{s0}}t_s^2 E_0^2[\Delta N\cos(2kn_{s0}d)]$$

where d is the thickness of the amorphous layer and the excess carrier concentration in the silicon under the amorphous layer is assumed to rise to a level $\Delta N$ in a distance very small compared to ½ $kn_{s0}$, where $n_{s0}$ is the index of refraction of the silicon and k is the wave-number, equal to $2\pi/\lambda$, where $\lambda$ is the wavelength. Here is it assumed that the index of refraction of the silicon and the amorphized layer are approximately equal, so that $n_{s0}$ represents both layers.

Figure 8B:
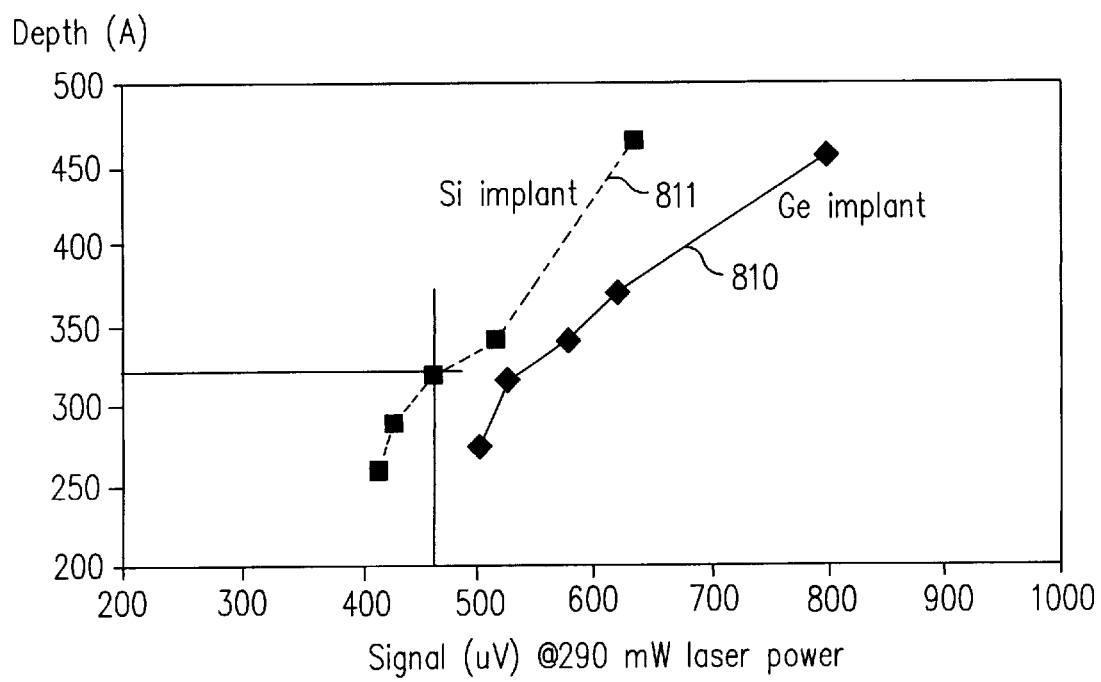
FIG. 8B illustrates, in a graph in accordance with the invention, the signal obtained in microvolts (at phase of 0°)at a generation laser power of 90 mW as a function of the thickness of the surface amorphous layer for various silicon and germanium ion implants.

The above relation indicates that the signal will vary as the cosine of the thickness of the layer multiplied by 2 kn. A calibration curve can therefore be established based on a measurement of reference samples to determine the signal as a function of depth. The curves in FIG. 8B show examples of calibration curves for Ge (line 810) and Si (line 811) [these designators have to be added to FIG. 8B; right now the lines are labeled "Si implant" and "Ge implant"] implants into silicon. These curves are created by measuring the signal on reference samples created by ion implanting silicon or germanium into silicon. The amorphization depth can be calculated using the TRIM, program, available from J. F. Ziegler, Mail Stop 28-024, IBM-Research, Yorktown, N.Y., 10598, USA. For example, suppose a measurement is made on a sample that has been implanted with silicon. At a generation laser power of 90 mW the measured signal is 460 microvolts. This would indicate an amorphization depth of 320 angstroms.

The above-described methods can be used to measure the active dopant profile in another special case, formed by the dose range of approximately $5\times10^{10}$ to $5\times10^{12}$ ions/cm$^2$ (often called the "low dose" range). Control of the dose of these implants is critical because they are used to adjust the turn-on voltage (threshold voltage) of field effect transistors. Small variations in these "low dose" implants can result in turn-on voltages that are out of the operating range of the integrated circuit.

Applicants recognize that such "low dose" implants cannot be measured by thermal wave methods of the type described by Opsal (U.S. Pat. No. 4,854,710) with high sensitivity, because such methods rely on the decay of the propagation of thermal waves due to the damage resulting from the ion implant. However, low dose implants create relatively little damage, and Opsal's thermal wave methods generally have very weak sensitivity in the low dose range (the sensitivity, defined as the percent change in signal divided by the percent change in dose, is typically about 0.2 for thermal wave methods; a sensitivity of 0.5 is usually considered the minimum usable level, and sensitivities >1.0 are considered desirable).

A significant reason for the weak sensitivity of Opsal's thermal wave methods is that they are sensitive to mobility but not lifetime. This may be shown as follows. The carrier distribution is a solution to the time dependent diffusion equation, $$\frac{\partial^2 n}{\partial z^2} - \frac{n}{D\tau} = \frac{1}{D}\frac{\partial n}{\partial t}$$

where n is the excess carrier concentration, D is the diffusion constant, with $$D = \left(\frac{k_b T}{q}\right)\mu,$$

where $k_b$ is Boltzmann's constant, T is the temperature, q the electron charge, and $\mu$ the mobility. $\tau$ is the lifetime. For a periodically excited carrier concentration at a radial frequency $\omega$, the carrier concentration is $n(z,t)=n(z)e^{j\omega t}$, where t is the time. This gives a diffusion equation of the form $$\frac{\partial^2 n}{\partial z^2} - n\left[\frac{1}{D\tau} + j\frac{\omega}{D}\right] = 0$$

At high frequencies, $\omega \gg 1/\tau$ (for an excess carrier lifetime of $10^{-4}$ seconds, this represents a frequency greater than about 15 kHz). The solution is of the form $n(z,t)=n_0 e^{j(\omega t - kz)}$, where $k^2=\omega/D$. This is a wave propagating solution whose propagation constant is a function of the mobility, since $$D = \left(\frac{k_b T}{q}\right)\mu.$$

This is the region where the thermal wave method operates, since that method relies on a propagating wave.

Conversely, at low frequencies, the solution is of the form $$n(z,t) = n_0 e^{\pm\frac{z}{\sqrt{D\tau}}} e^{j(\omega t)}.$$

This shows a static spatial variation that is a function of both mobility and lifetime. The import of this result is that the lifetime of a semiconductor is several orders of magnitude more sensitive to defect density than the mobility, so a measurement sensitive to lifetime will show greater sensitivity to the damage caused by low doses of ion implantation than a measurement sensitive to the mobility.

Therefore, there is a transition from a wave behavior to a diffusion behavior (that is sensitive to carrier lifetime) when $\omega=1/\tau$, i.e. when $f=(\frac{1}{2}\pi\tau)$. Therefore, in one embodiment, the modulation frequency is preselected to be any frequency in conformance with the formula $f \leq (\frac{1}{2}\pi\tau)$.

A graph illustrated in FIG. 9A shows the results of calculations based on a solution to the diffusion equation assuming the ion implanted layer at the surface has a reduced lifetime compared to the bulk silicon under the implanted region. The horizontal axis is the depth in microns and the vertical axis is the carrier concentration per cubic cm. Note that for small changes in lifetime in the implanted layer, the carrier concentration is nearly constant. However, as the lifetime in the implanted layer becomes shorter, the surface concentration starts to drop very quickly. Over this range, the surface concentration drops quickly. At a certain point—about $10^{-11}$ seconds in this model—the carrier concentration becomes relatively independent of lifetime again. However, the point of reflection shifts from the surface to the boundary between the implanted layer and the bulk silicon. In this regime, the signal levels off.

Another graph illustrated in FIG. 9B shows the signal for various low dose implants, including a variety of species (B—Boron, As—Arsenic, P—Phosphorous, and BF$_2$—Boron Fluoride) as a function of dose. For the lower doses, the signal is seen to drop relatively rapidly. For the higher doses, the signal flattens out. This is consistent with the above model. The signal in the steep part comes from the surface reflection—the first term in the parenthesis in equation 15. As the signal flattens and begins to come from reflection from the interface between the implant and the bulk, the interference term contributes. This explains why the signal changes phase, and is negative at the higher dose values.

The graph in FIG. 9B may be used to calibrate the measurement in a manner similar to that for the amorphous measurement. The signal as a function of dose is measured and stored as a graph similar to FIG. 9B. For example, a signal of 100 for a Boron implant corresponds to a dose of 5e11.

In one specific implementation, the following software is used to program computer 103C for finding a semiconductor property, namely the junction depth:

APPENDIX A

```
Attribute VB_Name = "SIGDEPTH"
'Module: SigDepth.bas
'Purpose: Finds junction depth by matching the power curve SIGNALs to the simulation
signals.
Option Explicit
Public Sub SigDepthShape(sig1 As Double, sig2 As Double, sig3 As Double,_
ContourFile As String, SkipShapes( ) As Double, MaxDep As Double,_
BestDepth As Double, bestshape As Long, beststdev As Double)
'
'This routine matches the signals of the power curve to the simulations
'
'Inputs:
'Sig1       double      signed signal at 10 mW = 8 mA
'Sig2       double      signed signal at 40 mW = 32 mA
```

APPENDIX A-continued

```
'Sig3           double        signed signal at 100 mW = 80 mA
'ContourFile string name of the file containing the
'                             two-dimensional depth shape lookup
'                             tables.
'SkipShapes double array of shapes to skip (easier than
'                             having to keep editing files!)
'                             if there is only one shape and it is negative, then
'                             REQUIRE that shape.
'MaxDep         maximum depth to return (possibly obsolete)
'
'Outputs:
'BestDepth      double        junction depth in microns
'BestShape      long          serial number of the shape
'BestStdev      double        standard deviation
Dim Nshapes As Integer            'number of shapes in lookup table
Dim ConDepths( ) As Double        'depths in the look-up table
                    'ConDepths(iDepth)
Dim ConSigs( ) As Double          '2-D look-up table
                    'ConSigs(iPower, iShape, iDepth)
Dim ConSerial( ) As Long          'Serial number
Dim FileGood As Boolean           'Tells if the contour file is good or not
Dim iShape As Integer, iDepth As Integer, iDepth2 As Integer    'loopers
Dim iFine As Integer, iSkip As Integer       'loopers
Dim GoingDown As Boolean      'these keep track of the trend of the Stdevs as we march
Dim LastStdev As Double       through the lookup table
Dim Stdev As Double         'the current figure of merit
Dim FineDepths( ) As Double, FineSigs( ) As Double      'Finer steps
Dim ThisShapeMin As Boolean 'keeps track of whether we have found a minimum for
this shape
Const Weighting = 1      'For easy switching in weightings, 1 = plain, 2 = fractional,
                                  3 = abs( )
'Initialize the variables
BestDepth = 0#
beststdev = 1E + 20
bestshape = 0
If MaxDep < 0.000001 Then MaxDep = 9999#
'Load the 2-dimensional contour table
Call LoadContours(ContourFile, ConDepths, ConSigs, ConSerial, Nshapes, FileGood)
If Not FileGood Then
    BestDepth = -99#
    bestshape = -99#
    beststdev = -99#
    GoTo Fini
End If
'Loop through each of the shapes:
For iShape = 1 To Nshapes
    here is where we skip shapes:
    For iSkip = LBound(SkipShapes) To UBound(SkipShapes)
        If iShape = SkipShapes(iSkip) Then GoTo NextShape
    Next iSkip
    'here is where we require shapes
    If L Bound(SkipShapes) = UBound(SkipShapes) And
SkipShapes(LBound(SkipShapes)) < 0 And iShape <>-
SkipShapes(LBound(SkipShapes))_
    Then GoTo NextShape
'This flag indicates that this shape has not found a minimum
'ThisShapeMin = False
'This flag indicates that things are getting better. (We continue until things get worse)
GoingDown = False
'Set the LastStdev to a code which means "there was no last stdev", that is,
' we are on the first one:
LastStdev = 99999#
'Run through the depths to see where the minima might be:
For iDepth = LBound(ConDepths) To UBound(ConDepths)
    'skip table entries which are 0
    If ConSigs(1, iShape, iDepth) = 0# Then GoTo NextDepth
    'find the Stdev: plain weighting:
    If Weighting = 1 Then
        Stdev = ((sig1 - ConSigs(1, iShape, iDepth))) ^2_
            + ((sig2 - ConSigs(2, iShape, iDepth))) ^2_
            + ((sig3 - ConSigs(3, iShape, iDepth))) ^2
        Stdev = Sqr(Stdev)
    End If
    If Weighting = 2 Then
        'find the Stdev: fractional weighting
        Stdev = ((sig1 - ConSigs(1, iShape, iDepth))/ConSigs(1, iShape, iDepth)) ^2_
            + ((sig2 - ConSigs(2, iShape, iDepth))/ConSigs(2, iShape, iDepth)) ^2_
            + ((sig3 - ConSigs(3, iShape, iDepth))/ConSigs(3, iShape, iDepth)) ^2
        Stdev = Sqr(Stdev)
```

APPENDIX A-continued

```
        End If
        If Weighting = 3 Then
        'find the Stdev: abs( ) weighting
        Stdev = (Abs(sig1 - ConSigs(1, iShape, iDepth)))_
            + (Abs(sig2 - ConSigs(2, iShape, iDepth)))_
            + (Abs(sig3 - ConSigs(3, iShape, iDepth)))
        End If
        'check to see if the stdev is going down (still)
        If LastStdev = 99999# Then
        'It's the first one we checked, pretend it is not useful
            LastStdev = Stdev
        Else
            'if the stdev is (still) getting smaller:
        If Stdev < LastStdev Then
            GoingDown = True
            LastStdev = Stdev
        Else
            'Stdev is still getting larger:
            If GoingDown = False Then
                LastStdev = Stdev
            Else
            'if the stdev is getting larger, but it used to be getting smaller, then
            'we have just passed the minimum, and we are ready to go to the next stage:
                'Find finer ConSigs around this depth:
                Call Finer(ConDepths, ConSigs, iShape, iDepth, FineDepths, FineSigs)
                For iFine = LBound(FineDepths) To UBound(FineDepths)
                'find the Stdev: plain weighting
                    If Weighting = 1 Then
                    Stdev = ((sig1 - FineSigs(1, iFine))) ^2_
                        + ((sig2 - FineSigs(2, iFine))) ^2_
                        + ((sig3 - FineSigs(3, iFine))) ^2
                    Stdev = Sqr(Stdev)
                    End If
                    If Weighting = 2 Then
                    'find the Stdev: fractional weighting
                        Stdev = ((sig1 - FineSigs(1, iFine))/FineSigs(1, iFine)) ^2_
                        + ((sig2 - FineSigs(2, iFine))/FineSigs(2, iFine)) ^2_
                        + ((sig3 - FineSigs(3, iFine))/FineSigs(3, iFine)) ^2
                    Stdev = Sqr(Stdev)
                    End If
                    If Weighting = 3 Then
                    'find the Stdev: abs( ) weighting
                        Stdev = (Abs(sig1 - FineSigs(1, iFine)))_
                        + (Abs(sig2 - FineSigs(2, iFine)))_
                        + (Abs(sig3 - FineSigs(3, iFine)))
                    End If
                    If Stdev < beststdev And FineDepths(iFine) < MaxDep Then
                        beststdev = Stdev
                        bestshape = ConSerial(iShape)
                        BestDepth = FineDepths(iFine)
                        ThisShapeMin = True
                    End If
                Next iFine
                GoingDown = False
            End If
        End If
    End If
NextDepth:
    Next iDepth
    'If we haven't found a minimum, then give each depth a chance to beat the lowest
    'so far:
    If Not ThisShapeMin Then
        For iDepth2 = LBound(ConDepths) To UBound(ConDepths)
            'skip table entries which are 0
            If ConSigs(1, iShape, iDepth2) = 0# Then GoToNextDepth2
            'find the Stdev: plain weighting:
            If Weighting = 1 Then
            Stdev = ((sig1 - ConSigs(1, iShape, iDepth2))) ^2_
                + ((sig2 - ConSigs(2, iShape, iDepth2))) ^2 _
                + ((sig3 - ConSigs(3, iShape, iDepth2))) ^2
            Stdev = Sqr(Stdev)
            End If
            If Weighting = 2 Then
            'find the Stdev: fractional weighting
            Stdev = ((sig1 - ConSigs(1, iShape, iDepth2))/ConSigs(1, iShape, iDepth2)) ^2_
                + ((sig2 - ConSigs(2, iShape, iDepth2))/ConSigs(2, iShape, iDepth2)) ^2_
                + ((sig3 - ConSigs(3, iShape, iDepth2))/ConSigs(3, iShape, iDepth2)) ^2
            Stdev = Sqr(Stdev)
            End If
```

APPENDIX A-continued

```
                If Weighting = 3 Then
                'find the Stdev: abs( ) weighting
                Stdev = (Abs(sig1 - ConSigs(1, iShape, iDepth2)))_
                    + (Abs(sig2 - ConSigs(2, iShape, iDepth2)))_
                    + (Abs(sig3 - ConSigs(3, iShape, iDepth2)))
                EndIf
                If Stdev < beststdev And ConDepths(iDepth2) < MaxDep Then
                    beststdev = Stdev
                    bestshape = ConSerial(iShape)
                    BestDepth = ConDepths(iDepth2)
                    End If
NextDepth2:
            Next iDepth2
        End If
NextShape:
Next iShape
Fini:
End Sub
Private Sub Finer(ConDepths( ) As Double, ConSigs( ) As Double, iShape As Integer,
iDepth As Integer,_
FineDepths( ) As Double, FineSigs( ) As Double)
'Makes finer steps of ConSigs and ConDepths
'Inputs:
'ConDepths(idepth)              The depths from the lookup table
'ConSigs(ipow, ishape, idepth) The sigs from the lookup table
'ishape                         Which shape we are on
'idepth                         the depth at which the Stdev started going up
'
'Outputs:
'FineDepths(1 to 201)           Depths at 1 A intervals
'FineSigs(ipow, 1 to 201)         Sigs at 1 A intervals
Const TwoPiWrap = 0.2164        'wrap-around point
Dim StartDepth As Double        'the starting point of the fine depths
Dim DeltaSig1 As Double, DeltaSig2 As Double, DeltaSig3 As Double ' steps in signal
Dim i As Integer        'looper
'INitialize the outputs
ReDim FineDepths(0 To 200)
ReDim FineSigs(1 To 3, 0 To 200)
'Find the starting depth
StartDepth = ConDepths(iDepth - 2)
'Find deltaSigs for the first 100 points:
DeltaSig1 = (ConSigs(1, iShape, iDepth - 1) - ConSigs(1, iShape, iDepth - 2))/100#
DeltaSig2 = (ConSigs(2, iShape, iDepth - 1) - ConSigs(2, iShape, iDepth - 2))/100#
DeltaSig3 = (ConSigs(3, iShape, iDepth - 1) - ConSigs(3, iShape, iDepth - 2))/100#
'Load the first hundred points:
For i = 0 To 100
    FineDepths(i) = StartDepth + i * 0.0001
    If FineDepths(i) > TwoPiWrap Then FineDepths(i) = FineDepths(i) - TwoPiWrap
    FineSigs(1, i) = ConSigs(1, iShape, iDepth - 2) + i * DeltaSig1
    FineSigs(2, i) = ConSigs(2, iShape, iDepth - 2) + i * DeltaSig2
    FineSigs(3, i) = ConSigs(3, iShape, iDepth - 2) + i * DeltaSig3
Next i
'Find deltaSigs for the next 100 points:
DeltaSig1 = (ConSigs(1, iShape, iDepth) - ConSigs(1, iShape, iDepth - 1))/100#
DeltaSig2 = (ConSigs(2, iShape, iDepth) - ConSigs(2, iShape, iDepth - 1))/100#
DeltaSig3 = (ConSigs(3, iShape, iDepth) - ConSigs(3, iShape, iDepth - 1))/100#
'Load the next hundred points:
For i = 101 To 200
    FineDepths(i) = StartDepth + i * 0.0001
    If FineDepths(i) > TwoPiWrap Then FineDepths(i) = FineDepths(i) - TwoPiWrap
    FineSigs(1, i) = ConSigs(1, iShape, iDepth - 1) + (i - 100) * DeltaSig1
    FineSigs(2, i) = ConSigs(2, iShape, iDepth - 1) + (i - 100) * DeltaSig2
    FineSigs(3, i) = ConSigs(3, ishape, iDepth - 1) + (i - 100) * DeltaSig3
Next i
End Sub
'========================
Public Sub LoadContours(FileName As String, Depths( ) As Double, Sigs( ) As Double,_
    SerialNo( ) As Long, Nshapes As Integer, FileGood As Boolean)
'This routine reads the simulation contours from a file and
'puts the data into big ol' arrays.
'
'Inputs:
'Filename     string    name of the file with the data
'
'Outputs:
'Depths( )       double     the depths in microns
'Sigs(pow,shape,depth) the signals from the simulations
'SerialNo(shape)       the serial number of the shape
'Nshapes       integer    number of shapes in table
```

APPENDIX A-continued

```
'
public
'
Dim Ndepths As Integer          'number of depths
Dim FileNum As Integer          'unit number to read file from
Dim AHeader As String           'for reading header info
Dim i As Integer         'looper
Dim iPow As Integer             'looper
Dim iShape As Integer           'looper
Dim iDep As Integer             'looper
Dim DumNum As Double            'placeholder
FileGood = True
FileNum = FreeFile
Open FileName For Input As #FileNum
'Read two header lines
Input #FileNum, AHeader
Input #FileNum, AHeader
'Read the number of shapes
Input #FileNum, Nshapes
'Another header line
Input #FileNum, AHeader
'Read the number of depths
Input #FileNum, Ndepths
'Now we can initialize the variables
ReDim Depths(1 To Ndepths)
ReDim Sigs(1 To 3, 1 To Nshapes, 1 To Ndepths)
ReDim SerialNo(1 To Nshapes)
'Another header line ("Key")
Input #FileNum, AHeader
'And Nshapes lines of header
For i = 1 To Nshapes
    Input #FileNum, DumNum, SerialNo(i)
Next i
'A blank line (make sure)
Input #FileNum, AHeader
If AHeader <> "" Then GoTo BadFileName
'Another header line
Input #FileNum, AHeader
'And now the depths:
For i = 1 To Ndepths
    Input #FileNum, Depths(i)
Next i
'Now read the signals for the three powers
For iPow = 1 To 3
    'a blank and a header
    Input #FileNum, AHeader
    If AHeader <> "" Then GoTo BadFileName
    Input #FileNum, AHeader
    'Nshapes rows of Ndepths depths:
    For iShape = 1 To Nshapes
        For iDep = 1 To Ndepths
            Input #FileNum, Sigs(iPow, iShape, iDep)
        Next iDep
    Next iShape
Next iPow
GoTo Fini
BadFileName:
' MsgBox FileName & "is bad. It will give goofy results"
    FileGood = False
    GoTo Fini
Fini:
Close FileNum
End Sub
```

The above software uses a power curve (see curve 404 in FIG. 4C) obtained by measurement of an interference signal (amplitude and phase, wherein phase is used to determine a sign to be used with the amplitude) as a function of the power of generation beam 151. Specifically, the software compares the measured power curve to a number of preexisting power curves that have been obtained by simulation (see curves 404–409 in FIG. 4E) to find a match. The matched power curve obtained by simulation determines the junction depth. The preexisting power curves are obtained as described above in reference to FIGS. 4D and 4E, and are referenced in the software as data in a "contour table."

Numerous modifications and adaptations of the above-described embodiments will become apparent to a person skilled in the art of semiconductor physics. For example, although computer 103C is described as being programmed with one or more specific equations, computer 103C can be programmed with other equations described herein, or with one or more equations that approximate any of the relations between material properties as described herein, for use with measurements performed by profiler 103 while creating a diffusive modulation of charge carriers in a wafer under measurement. For example, an approximate equation used by profiler 103 to measure a material property can be obtained by curve-fitting to measurement data from reference wafers, or by curve-fitting to data obtained from a numerical model, or both depending on the specific implementation.

Therefore, numerous such modifications and adaptations of the above-described embodiments are encompassed by the attached claims.

What is claimed is:

1. A method for performing a measurement in a region of a wafer having a plurality of charge carriers, the plurality consisting of a first number of charge carriers, the method comprising:

stimulating the region, the plurality consisting of a second number of charge carriers during the stimulating;

using a measurement device to obtain a measured value of a signal affected by the stimulating;

operating a simulator to generate a simulated value of the signal based on:
  (i) a predetermined profile of concentration of active dopants in the region; and
  (ii) conditions of the stimulating; and comparing the simulated value with the measured value to determine if the simulated value matches the measured value.

2. The method of claim 1 further comprising:

repeating the operating for a set of predetermined profiles including the predetermined profile to generate a set of simulated values including the simulated value;

repeating the comparing with each simulated value in the set to determine the simulated value closest to the measured value to be a match.

3. The method of claim 1 further comprising:

repeating the operating with a number of additional predetermined profiles until an additional simulated value and the measured value differ by less than a predetermined amount; and determining the additional simulated value to be a match.

4. The method of claim 1 further comprising:

computing a value of a property of the region based on the predetermined profile.

5. The method of claim 1 further comprising:

driving a control signal to a device selected from the group consisting of a wafer processing unit and an annealer based on a result of said comparing.

6. The method of claim 1 wherein:

the measurement device includes an interferometer; and the signal is an interference signal obtained by interference between:
  a reference beam; and
  a portion of a probe beam of electromagnetic radiation reflected by a plurality of excess carriers in the region, the plurality of excess carriers being created by the stimulating.

7. The method of claim 6 wherein:

the reference beam is formed by another portion of the probe beam that is reflected from a front surface of said substrate.

8. The method of claim 1 wherein:

the stimulating includes creating a plurality of excess carriers in the region, the number of excess carriers in the plurality being modulated in time at a predetermined frequency that is sufficiently small to ensure that a majority of carriers move out of the region by diffusion.

9. The method of claim 8 wherein:

the operating includes determining a profile of excess carriers as a function of depth in the substrate.

10. The method of claim 9 further comprising:

using the profile of excess carriers to determine the simulated value.

* * * * *